US008604916B2

(12) United States Patent
McNeely et al.

(10) Patent No.: US 8,604,916 B2
(45) Date of Patent: *Dec. 10, 2013

(54) ASSOCIATION OF SUPPORT SURFACES AND BEDS

(75) Inventors: Craig A. McNeely, Columbus, IN (US); Carl W. Riley, Milan, IN (US); Keith A. Huster, Sunman, IN (US); Irvin J. Vanderpohl, III, Greensburg, IN (US); Patricia A. Glidewell, Cary, NC (US); David C. Ferguson, Wake Forest, NC (US); Simeon Zhao, Apex, NC (US); Daleep Bhatia, Cary, NC (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/242,255

(22) Filed: Sep. 23, 2011

(65) Prior Publication Data
US 2012/0013452 A1 Jan. 19, 2012

Related U.S. Application Data

(63) Continuation of application No. 12/961,608, filed on Dec. 7, 2010, now Pat. No. 8,031,057, which is a continuation of application No. 11/846,906, filed on Aug. 29, 2007, now Pat. No. 7,868,740.

(51) Int. Cl.
*G08B 5/22* (2006.01)

(52) U.S. Cl.
USPC .............. 340/286.07; 340/539.12; 340/573.1; 705/2

(58) Field of Classification Search
USPC .................. 340/286.07, 539.12, 573.1; 705/2; 5/616
See application file for complete search history.

(56) References Cited

U.S. PATENT DOCUMENTS

| | | | |
|---|---|---|---|
| 2,330,356 A | 9/1943 | Belliveau |
| 2,335,524 A | 11/1943 | Lomax |
| 2,736,888 A | 2/1956 | McLain |
| 2,896,021 A | 7/1959 | Philipps |
| 3,098,220 A | 7/1963 | De Graaf |
| 3,439,320 A | 4/1969 | Ward |
| 3,478,344 A | 11/1969 | Schwitzgebel et al. |
| 3,553,383 A | 1/1971 | Rochtus |

(Continued)

FOREIGN PATENT DOCUMENTS

WO WO 02/091297 A1 11/2002
WO WO 2004/036390 A2 4/2004

*Primary Examiner* — Brent Swarthout
(74) *Attorney, Agent, or Firm* — Barnes & Thornburg LLP

(57) ABSTRACT

Systems, methods, beds, supports surfaces and machine readable medium for associating beds and support surface of a healthcare facility are disclosed. A surface association system for a healthcare facility may comprise a plurality of beds. The system may further comprise a computing device and a plurality of support surfaces to be placed upon beds of the plurality of beds. The computing device may associate a support surface of the plurality of support surfaces with a bed of the plurality of beds. The computing device may make the association based upon status data received from the plurality of beds and the plurality of support surfaces. The support surface and/or bed to be associated may initiate a surface association request. The computing device, in response to the surface association request, may request performance of one or more actions on the bed and/or support surface to be associated to identify the bed and/or support surface from the beds and support surfaces of the healthcare facility.

17 Claims, 14 Drawing Sheets

(56) References Cited

U.S. PATENT DOCUMENTS

| | | |
|---|---|---|
| 3,599,199 A | 8/1971 | Bunting |
| 3,599,200 A | 8/1971 | Bunting |
| 3,696,384 A | 10/1972 | Lester |
| 3,739,329 A | 6/1973 | Lester |
| 3,767,859 A | 10/1973 | Doering et al. |
| 3,805,265 A | 4/1974 | Lester |
| 3,913,153 A | 10/1975 | Adams et al. |
| 3,973,200 A | 8/1976 | Akerberg |
| 4,067,005 A | 1/1978 | Levy et al. |
| 4,150,284 A | 4/1979 | Trenkler et al. |
| 4,151,407 A | 4/1979 | McBride et al. |
| 4,183,015 A | 1/1980 | Drew et al. |
| 4,216,462 A | 8/1980 | McGrath et al. |
| 4,225,953 A | 9/1980 | Simon et al. |
| 4,228,426 A | 10/1980 | Roberts |
| 4,237,344 A | 12/1980 | Moore |
| 4,264,982 A | 4/1981 | Sakarya |
| 4,275,385 A | 6/1981 | White |
| 4,279,433 A | 7/1981 | Petaja |
| 4,298,863 A | 11/1981 | Natitus et al. |
| 4,331,953 A | 5/1982 | Blevins et al. |
| 4,356,475 A | 10/1982 | Neumann et al. |
| 4,418,334 A | 11/1983 | Burnett |
| 4,455,548 A | 6/1984 | Burnett |
| 4,489,387 A | 12/1984 | Lamb et al. |
| 4,495,495 A | 1/1985 | Ormanns et al. |
| 4,495,496 A | 1/1985 | Miller, III |
| 4,539,560 A | 9/1985 | Fleck et al. |
| 4,577,185 A | 3/1986 | Andersen |
| 4,578,671 A | 3/1986 | Flowers |
| 4,582,280 A | 4/1986 | Nichols et al. |
| 4,593,273 A | 6/1986 | Narcisse |
| 4,598,275 A | 7/1986 | Ross et al. |
| 4,601,064 A | 7/1986 | Shipley |
| 4,649,385 A | 3/1987 | Aires et al. |
| 4,680,790 A | 7/1987 | Packard et al. |
| 4,709,330 A | 11/1987 | Yokoi et al. |
| 4,740,788 A | 4/1988 | Konneker |
| 4,752,951 A | 6/1988 | Konneker |
| 4,792,798 A | 12/1988 | Wilowski |
| 4,795,905 A | 1/1989 | Zierhut |
| 4,814,751 A | 3/1989 | Hawkins et al. |
| 4,833,452 A | 5/1989 | Currier |
| 4,833,467 A | 5/1989 | Kobayashi et al. |
| 4,837,568 A | 6/1989 | Snaper |
| 4,853,692 A | 8/1989 | Wolk et al. |
| 4,899,135 A | 2/1990 | Ghahariiran |
| 4,947,152 A | 8/1990 | Hodges |
| 4,955,000 A | 9/1990 | Nastrom |
| 4,967,195 A | 10/1990 | Shipley |
| 4,990,892 A | 2/1991 | Guest et al. |
| 4,998,095 A | 3/1991 | Shields |
| 4,998,939 A | 3/1991 | Potthast et al. |
| 5,006,830 A | 4/1991 | Merritt |
| 5,027,314 A | 6/1991 | Linwood et al. |
| 5,041,086 A | 8/1991 | Koenig et al. |
| 5,062,151 A | 10/1991 | Shipley |
| 5,065,154 A | 11/1991 | Kaiser et al. |
| 5,086,290 A | 2/1992 | Murray et al. |
| 5,103,108 A | 4/1992 | Crimmins |
| 5,124,991 A | 6/1992 | Allen |
| 5,137,033 A | 8/1992 | Norton |
| 5,153,584 A | 10/1992 | Engira |
| 5,266,944 A | 11/1993 | Carroll et al. |
| 5,291,399 A | 3/1994 | Chaco |
| 5,319,355 A | 6/1994 | Russek |
| 5,319,363 A | 6/1994 | Welch et al. |
| 5,357,254 A | 10/1994 | Kah, Jr. |
| 5,375,604 A | 12/1994 | Kelly et al. |
| 5,396,224 A | 3/1995 | Dukes et al. |
| 5,396,227 A | 3/1995 | Carroll et al. |
| 5,416,695 A | 5/1995 | Stutman et al. |
| 5,434,775 A | 7/1995 | Sims et al. |
| 5,446,678 A | 8/1995 | Saltzstein et al. |
| 5,455,560 A | 10/1995 | Owen |
| 5,458,123 A | 10/1995 | Unger |
| 5,461,390 A | 10/1995 | Hoshen |
| 5,475,367 A | 12/1995 | Prevost |
| 5,534,851 A | 7/1996 | Russek |
| 5,537,459 A | 7/1996 | Price et al. |
| 5,548,637 A | 8/1996 | Heller et al. |
| 5,549,113 A | 8/1996 | Halleck et al. |
| 5,561,412 A | 10/1996 | Novak et al. |
| 5,568,119 A | 10/1996 | Schipper et al. |
| 5,576,952 A | 11/1996 | Stutman et al. |
| 5,579,001 A | 11/1996 | Dempsey et al. |
| 5,588,005 A | 12/1996 | Ali et al. |
| 5,594,786 A | 1/1997 | Chaco et al. |
| 5,621,388 A | 4/1997 | Sherburne et al. |
| 5,635,907 A | 6/1997 | Bernard et al. |
| 5,636,245 A | 6/1997 | Ernst et al. |
| 5,640,953 A | 6/1997 | Bishop et al. |
| 5,650,769 A | 7/1997 | Campana, Jr. |
| 5,650,770 A | 7/1997 | Schlager et al. |
| 5,664,270 A | 9/1997 | Bell et al. |
| 5,682,139 A | 10/1997 | Pradeep et al. |
| 5,686,888 A | 11/1997 | Welles, II et al. |
| 5,686,902 A | 11/1997 | Reis et al. |
| 5,687,734 A | 11/1997 | Dempsey et al. |
| 5,689,229 A | 11/1997 | Chaco et al. |
| 5,691,980 A | 11/1997 | Welles, II et al. |
| 5,699,038 A | 12/1997 | Ulrich et al. |
| 5,705,980 A | 1/1998 | Shapiro |
| 5,708,421 A | 1/1998 | Boyd |
| 5,713,856 A | 2/1998 | Eggers et al. |
| 5,719,761 A | 2/1998 | Gatti et al. |
| 5,731,757 A | 3/1998 | Layson, Jr. |
| 5,742,237 A | 4/1998 | Bledsoe |
| 5,751,246 A | 5/1998 | Hertel |
| 5,752,917 A | 5/1998 | Fuchs |
| 5,760,704 A | 6/1998 | Barton et al. |
| 5,767,791 A | 6/1998 | Stoop et al. |
| 5,781,442 A | 7/1998 | Engleson et al. |
| 5,793,290 A | 8/1998 | Eagleson et al. |
| 5,808,564 A | 9/1998 | Simms et al. |
| 5,812,056 A | 9/1998 | Law |
| 5,822,418 A | 10/1998 | Yacenda et al. |
| 5,822,544 A | 10/1998 | Chaco et al. |
| 5,838,223 A | 11/1998 | Gallant et al. |
| 5,844,488 A | 12/1998 | Musick |
| 5,867,821 A | 2/1999 | Ballantyne et al. |
| 5,877,675 A | 3/1999 | Rebstock et al. |
| 5,933,488 A | 8/1999 | Marcus et al. |
| 5,936,539 A | 8/1999 | Fuchs |
| 5,942,986 A | 8/1999 | Shabot et al. |
| 5,944,659 A | 8/1999 | Flach et al. |
| 5,963,137 A | 10/1999 | Waters, Sr. |
| 5,974,389 A | 10/1999 | Clark et al. |
| 5,991,728 A | 11/1999 | DeBusk et al. |
| 5,995,937 A | 11/1999 | DeBusk et al. |
| 6,014,633 A | 1/2000 | DeBusk et al. |
| 6,057,758 A | 5/2000 | Dempsey et al. |
| 6,057,782 A | 5/2000 | Koenig |
| 6,067,019 A | 5/2000 | Scott |
| 6,076,166 A | 6/2000 | Moshfeghi et al. |
| 6,085,493 A | 7/2000 | DeBusk et al. |
| 6,088,362 A | 7/2000 | Turnbull et al. |
| 6,093,146 A | 7/2000 | Filangeri |
| 6,097,308 A | 8/2000 | Albert et al. |
| 6,128,512 A | 10/2000 | Trompower et al. |
| 6,133,837 A | 10/2000 | Riley |
| 6,147,592 A | 11/2000 | Ulrich et al. |
| 6,183,417 B1 | 2/2001 | Geheb et al. |
| 6,208,250 B1 | 3/2001 | Dixon et al. |
| 6,241,668 B1 | 6/2001 | Herzog |
| 6,259,355 B1 | 7/2001 | Chaco et al. |
| 6,264,614 B1 | 7/2001 | Albert et al. |
| 6,279,183 B1 | 8/2001 | Kummer et al. |
| 6,287,253 B1 | 9/2001 | Ortega et al. |
| 6,302,844 B1 | 10/2001 | Walker et al. |
| 6,314,556 B1 | 11/2001 | DeBusk et al. |
| 6,320,510 B2 | 11/2001 | Menkedick et al. |
| 6,344,794 B1 | 2/2002 | Ulrich et al. |

(56) References Cited

U.S. PATENT DOCUMENTS

| | | |
|---|---|---|
| 6,348,777 B1 | 2/2002 | Brown et al. |
| 6,362,725 B1 | 3/2002 | Ulrich et al. |
| 6,364,834 B1 | 4/2002 | Reuss et al. |
| 6,398,727 B1 | 6/2002 | Bui et al. |
| 6,406,426 B1 | 6/2002 | Reuss et al. |
| 6,407,335 B1 | 6/2002 | Franklin-Lees et al. |
| 6,412,980 B1 | 7/2002 | Lounsberry et al. |
| 6,416,471 B1 | 7/2002 | Kumar et al. |
| 6,421,649 B1 | 7/2002 | Rattner |
| 6,439,769 B1 | 8/2002 | Polkus et al. |
| 6,441,742 B1 | 8/2002 | Lovely et al. |
| 6,442,290 B1 | 8/2002 | Ellis et al. |
| 6,445,299 B1 | 9/2002 | Rojas, Jr. |
| 6,450,956 B1 | 9/2002 | Rappaport et al. |
| 6,462,656 B2 | 10/2002 | Ulrich et al. |
| 6,486,792 B1 | 11/2002 | Moster et al. |
| 6,493,568 B1 | 12/2002 | Bell et al. |
| 6,494,831 B1 | 12/2002 | Koritzinsky |
| 6,510,344 B1 | 1/2003 | Halpern |
| 6,516,324 B1 | 2/2003 | Jones et al. |
| 6,526,310 B1 | 2/2003 | Carter et al. |
| 6,529,164 B1 | 3/2003 | Carter |
| 6,533,453 B1 | 3/2003 | Heidsieck et al. |
| 6,535,576 B2 | 3/2003 | Vafi et al. |
| 6,539,393 B1 | 3/2003 | Kabala |
| 6,544,173 B2 | 4/2003 | West et al. |
| 6,544,174 B2 | 4/2003 | West et al. |
| 6,551,243 B2 | 4/2003 | Bocionek et al. |
| 6,553,106 B1 | 4/2003 | Gould et al. |
| 6,554,174 B1 | 4/2003 | Aceves |
| 6,556,630 B1 | 4/2003 | Brinsfield et al. |
| 6,560,274 B1 | 5/2003 | Leitgeb et al. |
| 6,572,556 B2 | 6/2003 | Stoycos et al. |
| 6,575,901 B2 | 6/2003 | Stoycos et al. |
| 6,581,204 B2 | 6/2003 | DeBusk et al. |
| 6,584,182 B2 | 6/2003 | Brodnick |
| 6,584,454 B1 | 6/2003 | Hummel, Jr. et al. |
| 6,585,645 B2 | 7/2003 | Hutchinson |
| 6,589,170 B1 | 7/2003 | Flach et al. |
| 6,593,528 B2 | 7/2003 | Franklin-Lees et al. |
| 6,594,146 B2 | 7/2003 | Frangesch et al. |
| 6,594,519 B2 | 7/2003 | Stoycos et al. |
| 6,600,421 B2 | 7/2003 | Freeman |
| 6,603,494 B1 | 8/2003 | Banks et al. |
| 6,609,115 B1 | 8/2003 | Mehring et al. |
| 6,616,606 B1 | 9/2003 | Petersen et al. |
| 6,622,088 B2 | 9/2003 | Hood |
| 6,640,246 B1 | 10/2003 | Gary, Jr. et al. |
| 6,643,238 B2 | 11/2003 | Nakajima |
| 6,650,346 B1 | 11/2003 | Jaeger et al. |
| 6,659,947 B1 | 12/2003 | Carter et al. |
| 6,665,385 B2 | 12/2003 | Rogers et al. |
| 6,665,820 B1 | 12/2003 | Frowein et al. |
| 6,669,630 B1 | 12/2003 | Joliat et al. |
| 6,671,547 B2 | 12/2003 | Lyster et al. |
| 6,671,563 B1 | 12/2003 | Engelson et al. |
| 6,685,633 B2 | 2/2004 | Albert et al. |
| 6,689,091 B2 | 2/2004 | Bui et al. |
| 6,694,367 B1 | 2/2004 | Miesbauer et al. |
| 6,694,509 B1 | 2/2004 | Stoval et al. |
| 6,697,765 B2 | 2/2004 | Kuth |
| 6,707,476 B1 | 3/2004 | Hochstedler |
| 6,714,913 B2 | 3/2004 | Brandt et al. |
| 6,721,818 B1 | 4/2004 | Nakamura |
| 6,726,634 B2 | 4/2004 | Freeman |
| 6,727,818 B1 | 4/2004 | Wildman et al. |
| 6,731,311 B2 | 5/2004 | Bufe et al. |
| 6,731,989 B2 | 5/2004 | Engleson et al. |
| 6,740,033 B1 | 5/2004 | Olejniczak et al. |
| 6,749,566 B2 | 6/2004 | Russ |
| 6,751,630 B1 | 6/2004 | Franks et al. |
| 6,754,545 B2 | 6/2004 | Haeuser et al. |
| 6,754,883 B2 | 6/2004 | DeBusk et al. |
| 6,759,959 B2 | 7/2004 | Wildman |
| 6,763,541 B2 | 7/2004 | Mahoney et al. |
| 6,771,172 B1 | 8/2004 | Robinson et al. |
| 6,773,396 B2 | 8/2004 | Flach et al. |
| 6,778,225 B2 | 8/2004 | David |
| 6,781,517 B2 | 8/2004 | Moster et al. |
| 6,784,797 B2 | 8/2004 | Smith et al. |
| 6,791,460 B2 | 9/2004 | Dixon et al. |
| 6,792,396 B2 | 9/2004 | Inda et al. |
| 6,801,227 B2 | 10/2004 | Bocionek et al. |
| 6,807,543 B2 | 10/2004 | Muthya |
| 6,825,763 B2 | 11/2004 | Ulrich et al. |
| 6,826,578 B2 | 11/2004 | Brackett et al. |
| 6,828,992 B1 | 12/2004 | Freeman et al. |
| 6,829,796 B2 | 12/2004 | Salvatini et al. |
| 6,830,549 B2 | 12/2004 | Bui et al. |
| 6,832,199 B1 | 12/2004 | Kucek et al. |
| 6,840,117 B2 | 1/2005 | Hubbard, Jr. |
| 6,847,814 B1 | 1/2005 | Vogeleisen |
| 6,868,256 B2 | 3/2005 | Dooley et al. |
| 6,871,211 B2 | 3/2005 | Labounty et al. |
| 6,873,884 B2 | 3/2005 | Brackett et al. |
| 6,876,985 B2 | 4/2005 | Kawanaka |
| 6,885,288 B2 | 4/2005 | Pincus |
| 6,891,909 B2 | 5/2005 | Hurley et al. |
| 6,904,161 B1 | 6/2005 | Becker et al. |
| 6,909,995 B2 | 6/2005 | Shiraishi |
| 6,912,549 B2 | 6/2005 | Rotter et al. |
| 6,915,170 B2 | 7/2005 | Engleson et al. |
| 6,925,367 B2 | 8/2005 | Fontius |
| 6,930,878 B2 | 8/2005 | Brackett et al. |
| 6,987,448 B2 | 1/2006 | Catton et al. |
| 7,068,143 B2 | 6/2006 | Doering et al. |
| 7,319,386 B2 | 1/2008 | Collins et al. |
| 7,461,425 B2 * | 12/2008 | Chambers et al. ................ 5/690 |
| 7,852,208 B2 * | 12/2010 | Collins et al. ............ 340/539.12 |
| 7,868,740 B2 * | 1/2011 | McNeely et al. ........ 340/286.07 |
| 8,031,057 B2 * | 10/2011 | McNeely et al. ........ 340/286.07 |
| 2001/0050610 A1 | 12/2001 | Gelston |
| 2001/0051765 A1 | 12/2001 | Walker et al. |
| 2002/0014951 A1 | 2/2002 | Kramer et al. |
| 2002/0044043 A1 | 4/2002 | Chaco et al. |
| 2002/0044059 A1 | 4/2002 | Reeder et al. |
| 2002/0067273 A1 | 6/2002 | Jaques et al. |
| 2002/0070867 A1 | 6/2002 | Conway et al. |
| 2002/0080037 A1 | 6/2002 | Dixon et al. |
| 2002/0103674 A1 | 8/2002 | Reeder et al. |
| 2002/0151990 A1 * | 10/2002 | Ulrich et al. .................... 700/65 |
| 2002/0173991 A1 | 11/2002 | Avitall |
| 2002/0186136 A1 | 12/2002 | Schuman |
| 2002/0196141 A1 | 12/2002 | Boone et al. |
| 2003/0010345 A1 | 1/2003 | Koblasz et al. |
| 2003/0028449 A1 | 2/2003 | Heinen et al. |
| 2003/0030569 A1 | 2/2003 | Ulrich et al. |
| 2003/0052787 A1 | 3/2003 | Zerhusen et al. |
| 2003/0074222 A1 | 4/2003 | Rosow et al. |
| 2003/0146835 A1 | 8/2003 | Carter |
| 2003/0149598 A1 | 8/2003 | Santoso et al. |
| 2003/0176798 A1 | 9/2003 | Simon |
| 2003/0206116 A1 | 11/2003 | Weiner et al. |
| 2004/0183681 A1 | 9/2004 | Smith |
| 2004/0183684 A1 | 9/2004 | Callaway |
| 2004/0186358 A1 | 9/2004 | Chernow et al. |
| 2004/0193449 A1 | 9/2004 | Wildman et al. |
| 2005/0035862 A1 | 2/2005 | Wildman et al. |
| 2005/0219059 A1 | 10/2005 | Ulrich et al. |
| 2005/0242946 A1 | 11/2005 | Hubbard, Jr. et al. |
| 2006/0179571 A1 | 8/2006 | Newkirk |
| 2006/0271207 A1 | 11/2006 | Shaw |
| 2006/0279427 A1 * | 12/2006 | Becker et al. ............... 340/573.4 |
| 2007/0010719 A1 | 1/2007 | Huster et al. |
| 2007/0141869 A1 | 6/2007 | McNeely et al. |
| 2009/0056027 A1 | 3/2009 | Ball et al. |
| 2009/0063183 A1 | 3/2009 | McNeely et al. |
| 2011/0072583 A1 | 3/2011 | McNeely et al. |
| 2011/0074571 A1 * | 3/2011 | Collins et al. ............. 340/539.12 |

* cited by examiner

ASSOCIATION OF SUPPORT SURFACES AND BEDS

CROSS-REFERENCE TO RELATED APPLICATIONS

This application is a continuation of U.S. application Ser. No. 12/961,608, filed, Dec. 7, 2010, which issued as U.S. Pat. No. 8,031,057, which is a continuation of U.S. application Ser. No. 11/846,906, filed Aug. 29, 2007, which issued as U.S. Pat. No. 7,868,740, each of which is hereby incorporated by reference herein.

BACKGROUND OF THE INVENTION

Some hospital beds are configured to communicate information to a nurse call system. Such nurse call systems typically have a computer at a remote nurse's station with a display on which information concerning bed status is shown. One or more nurse call buttons are sometimes provided on a hospital bed, such as on one or more siderails of the bed and/or on a handheld pendant that is coupled to the bed. A patient may press one of the nurse call buttons to request to speak with a nurse. A nurse at the remote nurse's station and the patient may communicate with each other over a two-way communications link which includes audio circuitry, such as a microphone and a speaker included on the bed or mounted on a room wall near the bed. In addition, the nurse at the remote nurse's station may use the computer to establish a two-way communications link between the remote nurse's station and a caregiver at some other location in a healthcare facility and/or between the patient placing the nurse call and a caregiver at some other location in the healthcare facility.

Hospital beds that connect to nurse call systems, typically do so via a wired connection established by a nurse call cable that extends between the bed and an interface unit having a jack mounted on a wall or headwall unit in the hospital room in which the bed is situated. Typically, a power cord from the bed also plugs into a power outlet on the wall or headwall unit. Before the bed is moved from one location to another in a healthcare facility, the nurse call cable and the power cord need to be unplugged. Caregivers sometimes forget to unplug the nurse call cable resulting in damage to the nurse call cable when the bed is wheeled away from the wall. When the bed arrives at its new location, the caregivers need to remember to plug in both the power cord and the nurse call cable. When the nurse call cable is unplugged, bed status data is no longer communicated to the nurse call system. In addition, many prior art nurse call systems are configured as local area networks (LAN's) which require the installation in the healthcare facility of the associated network infrastructure, such as the bed interface units and the wiring from the bed interface units to the computer at the remote nurse's station.

Support surfaces such as, for example, mattresses may be placed upon decks of the hospital beds. The support surfaces often include an array of different functions used to care and/or treat various ailments and/or conditions of a patient. Hospital beds are often configured to receive support surfaces from different manufactures and/or different models from the same manufacture. As a result, a healthcare facility may include numerous different combinations of hospital bed models and support surface models.

SUMMARY OF THE INVENTION

The present invention may comprise a system, apparatus and/or method that may have one or more of the following features and/or steps, which alone or in any combination may comprise patentable subject matter:

A surface association system for a healthcare facility may comprise a plurality of beds. The system may further comprise a computing device and a plurality of support surfaces to be placed upon beds of the plurality of beds. The computing device may associate a support surface of the plurality of support surfaces with a bed of the plurality of beds. The computing device may make the association based upon status data received from the plurality of beds and the plurality of support surfaces.

In one embodiment, the bed to be associated may initiate a surface association request. The computing device, in response to the surface association request initiated by the bed, may request performance of one or more actions on the support surface to be associated with the bed in order to identify the support surface. The support surface to be associated may provide the computing device with data indicative of the one or more actions in response to the one or more actions being performed.

The system may further comprise a plurality of location transmitters. Each location transmitter may transmit a location identifier signal comprising a location identifier indicative of a location of the respective location transmitter. Each of the plurality of beds may include a location receiver to receive the location identifier. The computing device may associate the support surface of the plurality of support surfaces with the bed of the plurality of beds based upon the location identifier of the bed. Each of the plurality of surfaces may also include a location receiver to receive the location identifier. The computing device may associate the bed of the plurality of beds with the support surface of the plurality of support surfaces based upon the location identifier of the support surface.

A method for associating a bed of a plurality of beds and a support surface of a plurality of support surfaces is also disclosed. The method may comprise receiving data from the plurality of beds and the plurality of support surfaces. The method also may comprise determining that a support surface of the plurality of support surfaces is placed upon a bed of the plurality of beds based upon the data received from the plurality of beds and the plurality of support surfaces, and updating data to associate the support surface and the bed. The method may further determine that the support surface is placed upon the bed based upon a location identifier of the support surface and a location identifier of the bed.

In one embodiment, the method may request a user to perform one or more actions upon the bed to identify the bed of the plurality of beds. The method may then determine that the support surface of the plurality of support surfaces is placed upon the bed of the plurality of beds based upon data that indicates the user performed the one or more actions upon the bed.

In another embodiment, the method may request a user to perform one or more actions upon the support surface to identify the support surface. The method may then determine that the support surface of the plurality of support surfaces is placed upon the bed of the plurality of beds based upon data that indicates the user performed the one or more actions upon the support surface.

Embodiments of the method may further comprise receiving location identifiers for the plurality of beds and the plurality of support surfaces. The method may then determine that the support surface is placed upon the bed based upon at least a portion of the location identifiers received for the plurality of beds and the plurality of support surfaces.

Other embodiments may include transmitting location identifiers from location transmitters located throughout a healthcare facility to the plurality of beds and/or the plurality of support surfaces. The method may then determining that the support surface is placed upon the bed based upon at least a portion of the location identifiers received for the plurality of beds and/or the plurality of support surfaces.

A bed for use in a healthcare facility comprising a plurality of location transmitters and a network is also described. The bed may comprise a deck to receive a support surface and a location receiver to receive a location identifier signal from a location transmitter of the plurality of location transmitters of the healthcare facility. The bed may have a network interface to establish a communications link between the bed and the network. The bed may also have a communications interface to establish a communications link between the bed and a support surface that has been placed into position upon the deck of the bed. The bed may also have a user interface having a plurality of user inputs to control operation of the bed. The user interface may also have one or more user inputs to initiate a request to associate a support surface to the bed. The user interface may also request one or more actions be performed upon the support surface and the one or more actions may selected to identify the support surface from a plurality of support surfaces.

The bed may also have control circuitry to control operation of the bed and to control the transfer of data between the bed and the network of the healthcare facility. The control circuitry may control operation of the support surface based upon data received from the network via the network interface by providing control words to the support surfaces via the communications interface. The control circuitry may initiate a request to associate a support surface to the bed in response to one or more actions performed upon the bed. In one embodiment, the one or more actions may include actions beyond activating user inputs of the user interface.

A support surface is described for use in a healthcare facility comprising a plurality of location transmitters and a network. The support surface may be placed upon a deck of a bed and may include a location receiver to receive a location identifier signal from a location transmitter of the plurality of location transmitters. The support surface may include a communications interface and a network interface. The communications interface may establish a communications link between the support surface and the bed upon which the support surface has been placed. The network work interface may establish a communications link between the support surface and the network.

The support surface may also comprise a user interface. The user interface may include a plurality of user inputs to control operation of the support surface. The user interface may also include one or more user inputs to initiate a request to associate a support surface to the bed. The user interface may requests that one or more actions be performed upon the bed to be associated with the support surface to identify the bed from the plurality of beds of the healthcare facility.

The support surface may include control circuitry to control operation of the support surface and to control the transfer of data between the bed and the network of the healthcare facility. The control circuitry may control operation of the bed based upon data received from the network via the network interface by providing control words to the bed via the communications interface. The control circuitry may initiate a request to associate the support surface to the bed in response to one or more actions performed upon the support surface and/or bed. The one or more actions may includes actions beyond activating user inputs of the user interface.

A machine readable medium for associating beds and supports surfaces is also described herein. The machine readable medium may comprise a plurality of instructions, that in response to being executed, result in a device providing an interface to receive user input that identifies a bed of a healthcare facility and a location of the healthcare facility, and updating data to reflect the bed being associated with the location of the healthcare facility in response to receiving user input that requests the bed be associated with the location. The plurality of instructions may further result in the device providing the interface to further receive user input that identifies a support surface of the healthcare facility, and updating data to further reflect the support surface being associated with the bed in response to receiving user input that requests the support surface be associated with the bed. The instructions may also result in the device providing the interface to receive user input that identifies a previously associated bed, surface and location, and updating data to reflect that the previously associated bed, surface and location are no longer associated in response to user input that requests the bed, surface and location be unassociated.

Additional features, which alone or in combination with any other feature(s), such as those listed above, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures, in which.

DETAILED DESCRIPTION OF THE DRAWINGS

Embodiments contemplated by this disclosure may be implemented in hardware, firmware, software, or any combination thereof. Embodiments disclosed herein may also be implemented as instructions stored on a machine-readable medium, which may be read and executed by one or more processors. A machine-readable medium may include any mechanism for storing information in a form readable by a machine (e.g., a computing device). For example, a machine-readable medium may include read only memory (ROM); random access memory (RAM); magnetic disk storage media; optical storage media; flash memory devices; and others.

Figure 1:
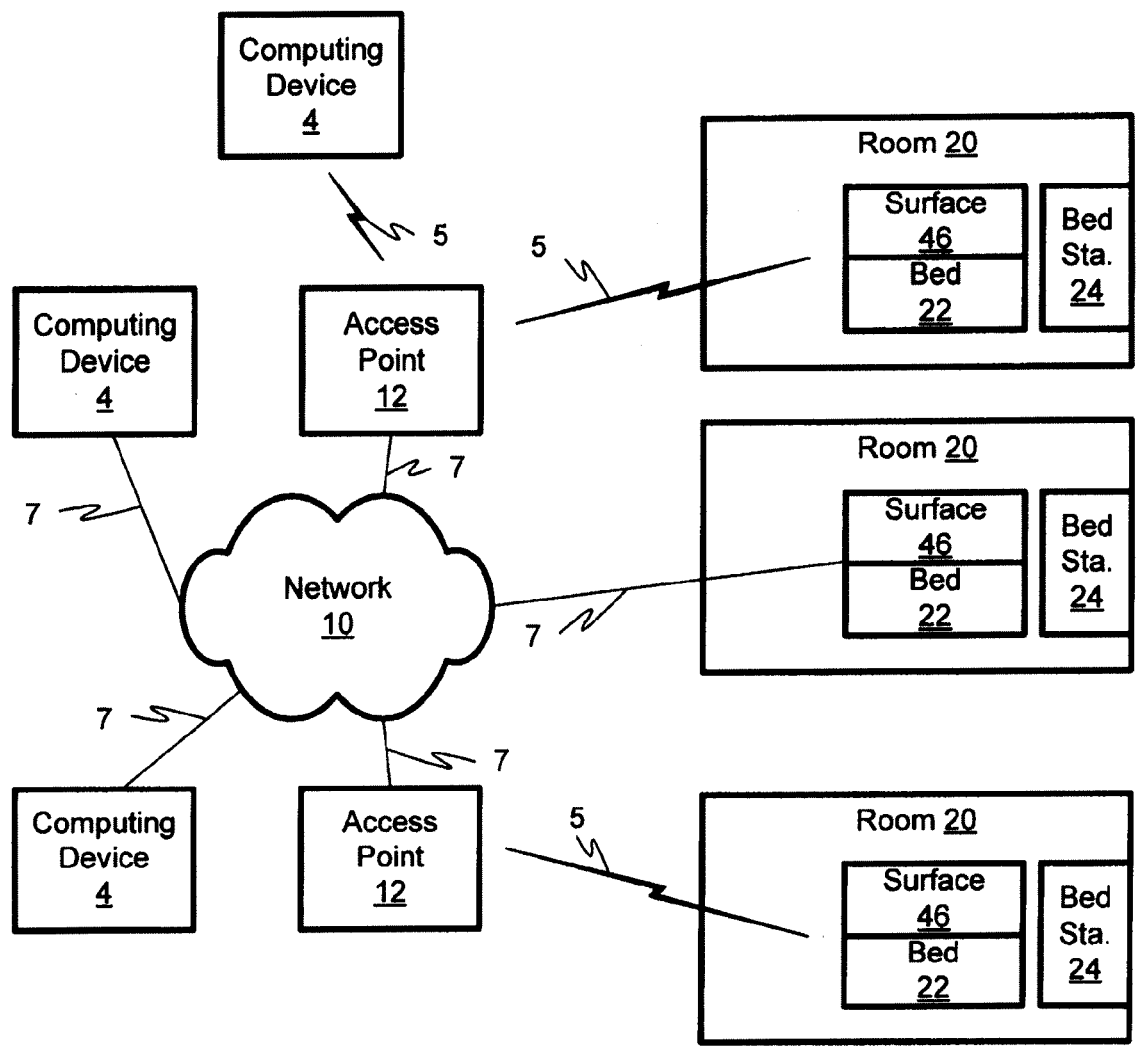
FIG. 1 is a block diagram showing computing devices, a network, and network access points of a healthcare facility as well as rooms, beds, supports surfaces and bed stations of the healthcare facility.

The following description describes techniques for associating a support surface such as a mattress to a hospital bed and/or associating a hospital bed with a support surface. Such techniques may be incorporated into a surface association system of a healthcare facility such as the healthcare facility shown diagrammatically in FIG. 1. As shown, the healthcare facility may comprise one or more computing devices 4 coupled to a network 10 via wireless connections 5 and/or wired connections 7. In support of wireless connections, the network 10 may comprise one or more wireless access points, bridges, proxy, switches, and/or routers 12 that provide devices such as computing devices 4 with wireless access to the network 10 and devices connected thereto. While the terms wireless access point, bridge, switches, and routers are used in the art to refer to different types of wireless devices, all such devices generally provide wireless access to a network. Thus, herein the term "access point" 12 is used to broadly refer to any such wireless device that provides computing devices 4, beds 22, support surfaces 46, and/or other devices wireless access to the network 10.

Each computing device 4, in one embodiment, provides the network 10 and devices connected thereto with one or more healthcare support services. Such healthcare support services may include, for example, a nurse call system, an admission-discharge-tracking (ADT) system, an electronic medical records (EMR) system, a workflow system, a medical records archiving system, a surface association system, and the like. As explained in greater detail below, one or more of the computing devices 104 includes software and/or firmware that, in response to being executed, results in one or more computing devices 104 providing the healthcare facility with a surface association service. The surface association service associates beds 22 with surfaces 46 and/or surfaces 46 with beds 22 based upon data received from the beds 22 and/or surfaces 46. Furthermore, the surface association service in some embodiments associates the beds 22 and/or surfaces 46 with locations in the healthcare facility based upon the data received from the beds 22 and/or surfaces 46.

As shown, the healthcare facility comprises several rooms 20 with bed stations 24. The bed stations 24 include power outlets, audio stations, and various other equipment and/or ports for connecting equipment used to care for a patient lying in a corresponding bed 22. While FIG. 1 only depicts rooms 20 having a single bed 22, surface 46 and station 24, the healthcare facility may comprise rooms 20 having one, two, three or more stations 24 in order to support one, two, three or more beds/surfaces per room 20.

Figure 2:
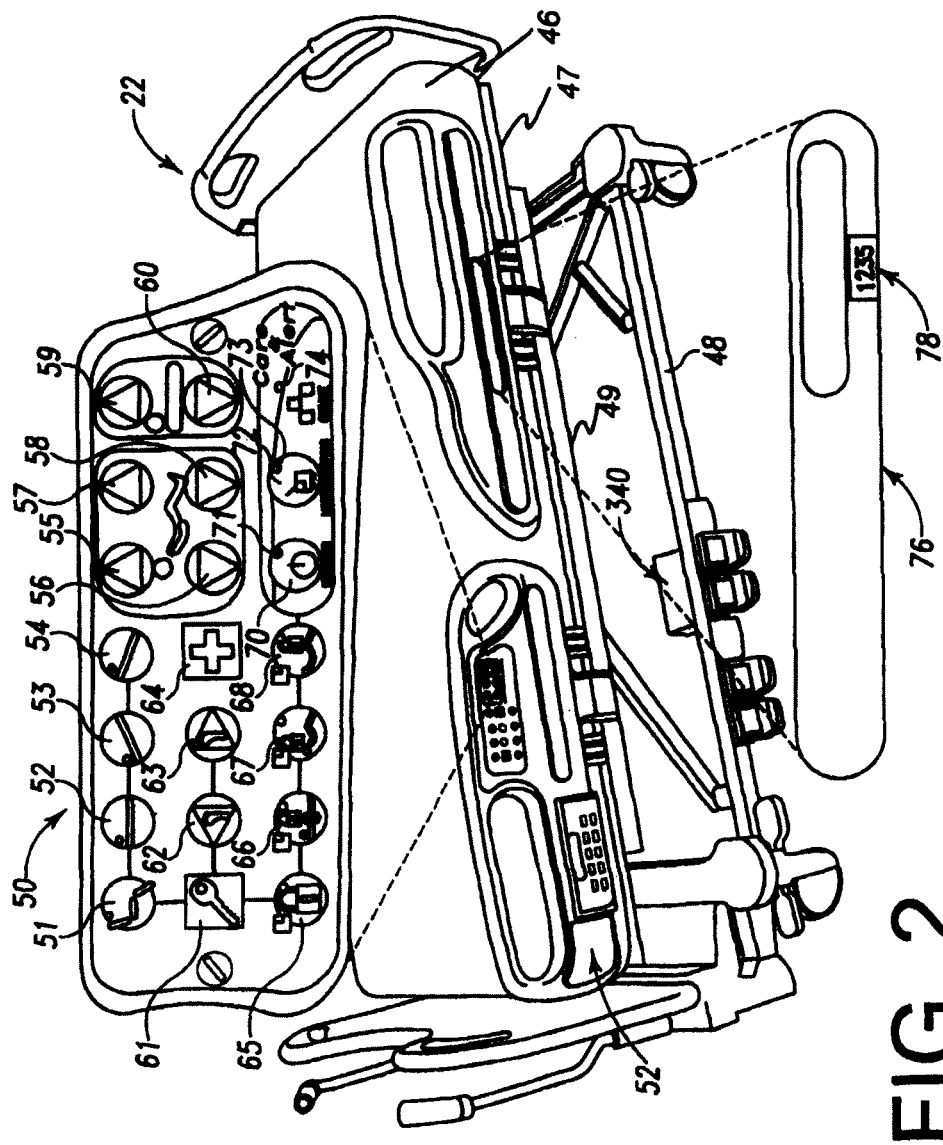
FIG. 2 is a perspective view of an embodiment of a hospital bed, with one enlarged portion of the view showing a user interface including LED's to indicate whether or not wireless communications are enabled, whether or not wireless communications are online, and whether or not housekeeping has been summoned to clean the associated bed and/or hospital room, and another enlarged portion of the view showing a label having bed ID data.

Referring now to FIG. 2, an embodiment of hospital bed 22 and support surface 46 is shown. The hospital bed 22 comprises a network interface 340 mounted to a base frame 48 of the hospital bed 22. In other embodiments, the network interface 340 may be mounted to bed 22 at other locations. Hospital bed 22 also has a user interface 50 accessible on the outwardly facing side of a siderail 52 of the hospital bed 22. In FIG. 2, an enlarged view of user interface 50 is shown so the various indicia associated with various user inputs (control buttons in the shown embodiment) can be seen more easily. Various buttons that are pressed to control associated functions of hospital bed 22 are included on user interface 50. These buttons include the following: a chair button 51 to articulate a support deck 47 upon which support surface 46 rests into a chair position; a "go to flat" button 52 to move the support deck 47 into a flat position; a Trendelenburg button 53 to tilt the support deck 47 into a Trendelenburg position; a reverse Trendelenburg button 54 to tilt the support deck 47 into a reverse Trendelenburg position; a head up button 55 to pivot a head section of the support deck 47 upwardly, a head down button 56 to pivot the head section of the support deck 47 downwardly; a knee up button 57 to pivot a thigh section of the support deck 47 upwardly; a knee down button 58 to pivot the thigh section of the support deck 47 downwardly; a raise button 59 to raise the support deck 47 and an upper frame 49 carrying the support deck 47 upwardly relative to base frame 48; a lower button 60 to lower the support deck 47 and the upper frame 49 downwardly relative to base frame 48; a key button 61 that is pressed to enable the use of other buttons for certain bed functions; a foot retract button 62 to shorten a foot section of the mattress support deck 47; a foot extend button 63 to lengthen the foot section of the support deck 47; a nurse call button 64 to place a nurse call to a remote nurse call computer; a lock button 65 that is pressed simultaneously with other buttons to lock or unlock certain bed functions; a hi/lo motor lockout button 66 to lock out hi/lo motors of bed 22 to prevent the upper frame 49 and support deck 47 from being raised and lowered relative to base frame 48; a head motor lockout 67 to lock out a head section actuator from raising and lowering the head section of the support deck 47; and a thigh motor lockout 68 to lock out a thigh section motor from raising and lowering a thigh section of the support deck 47.

The support surface 46, when placed into position, rests upon the support deck 47 of hospital bed 22. A particular hospital bed 22 may be compatible with multiple types of supports surfaces 46 such as, for example, air mattresses including therapy mattresses of various types (e.g. lateral rotation mattresses, alternating pressure mattresses, low air loss mattresses, and so on), and other specialty mattresses that each provide various features to support patient care. The support surface 46 may comprise a control unit in a housing that couples to a footboard of a bed 22, or to some other portion of the bed 22. Such surface control units typically have pumps, compressors, blowers, valves, manifolds, and the like, as well as electrical control circuitry and user interfaces to provide control signals to the various other components housed in the control unit. Other support surfaces 46 may integrate some or all of the components of such a control unit into a portion of the surface, such as a foot section of the surface.

The hospital bed 22 further has a label 76 with bed ID data 78 thereon as shown in FIG. 2. In some embodiments, the bed ID data 78 is the MAC address assigned to the network interface of the bed 22. It should be appreciated that the support surface 46 may have a label similar to label 76 with surface ID data thereon. Further, like the bed ID data 78 the, surface ID data may include a MAC address assigned to the network interface of the support surface 46.

In connection with the wireless communication capability provided by the network interfaces of bed 22 and/or support surface 46 of FIG. 2, the user interface 50 has an enabled button 70 with an indicator 71, a housekeeping button 72 with an indicator 73, and an on-line indicator 74. In some embodiments, indicators 71, 73, 74 are light emitting diodes (LED's), such as LED's that are operable to shine red, green, and/or amber. For example, when bed 22 is successfully wirelessly communicating with an access point 12 of the network 10, indicator 74 may shine green and when no wireless communications are taking place, indicator 74 may shine red. On-line indicator 74 may shine yellow during a time period in which bed 22 is attempting to reestablish wireless communication with network 10 after wireless communications are initially lost. In other embodiments, one or more of indicators 71, 73, 74 may comprise single color LED's or other types of indications including messages on electronic display screens.

Successive presses of enabled button 70 enable and suspend a Care Alert template for bed 22. Successive presses of housekeeping button 72 makes a housekeeping request and cancels the housekeeping request. However, in order for presses of buttons 70, 72 to be effective, key button 61 is first be pressed and held for a predetermined period of time, such as one second. Once button 261 has been pressed for the predetermined period of time, then buttons 70, 72 may be pressed within another predetermined period of time, such as 20 seconds, to change the state of the associated feature of buttons 70, 72. This control scheme for buttons 61, 70, 72 prevents inadvertent presses of buttons 70, 72 from changing the associated state of the associated feature. In some embodiments, Care Alerts enabled indicator 71 of Care Alerts enable button 70 shines green when the Care Alert template associated with bed 22 is enabled, blinks or flashes green when the Care Alert template associated with bed 22 is suspended, and is turned off when no Care Alert template is set up for bed 22. In some embodiments, the housekeeping indicator 73 shines green when a housekeeping request has been made by a press of housekeeping button 72 and is turned off when no housekeeping request has been made or after a housekeeping request has been canceled. The housekeeping request may be canceled before or after a staff member actually cleans the bed and/or room.

Figure 3A:
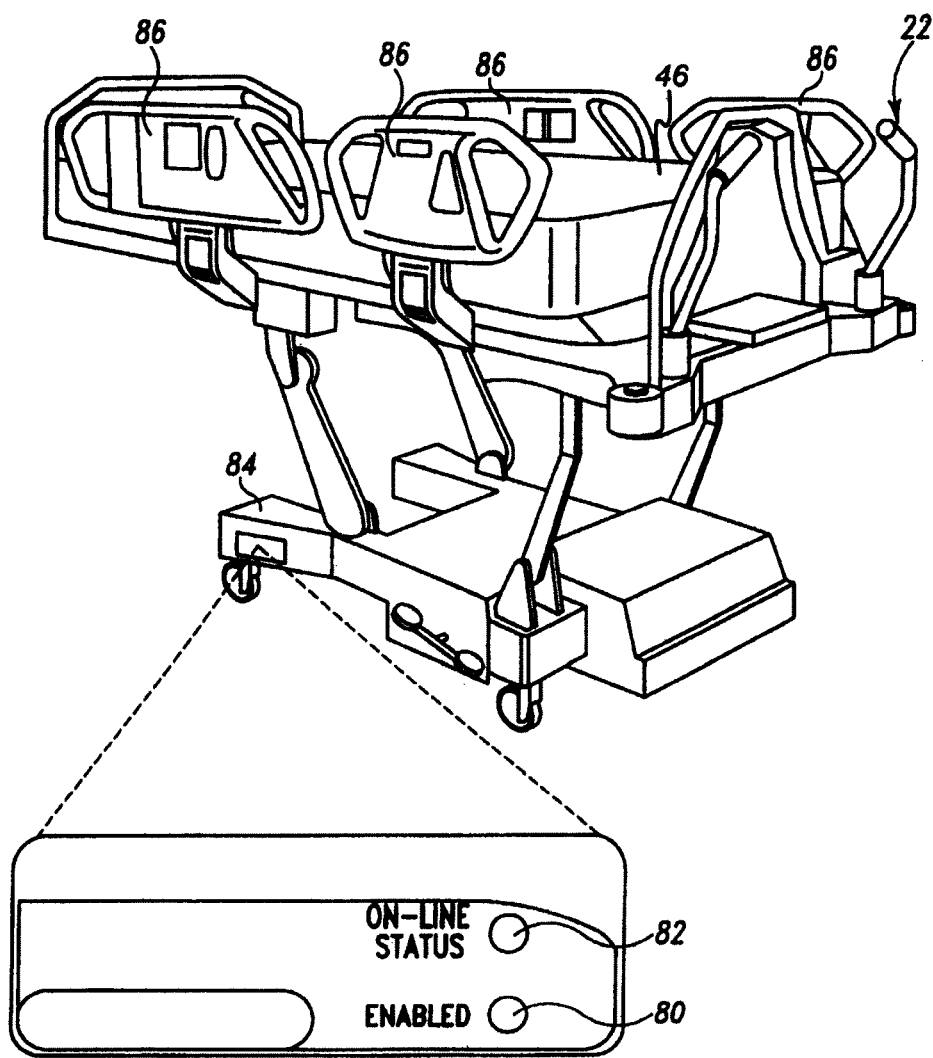
FIGS. 3A and 3B are perspective views of beds according to another embodiment, with one enlarged portion of the view associated with one of the beds showing indicator LED's on a base frame of the bed to indicate whether or not wireless communications are enabled and whether or not wireless communications are online, and another enlarged portion of the view associated with another of the beds showing a label having bed ID data and a bar code.
Figure 3B:
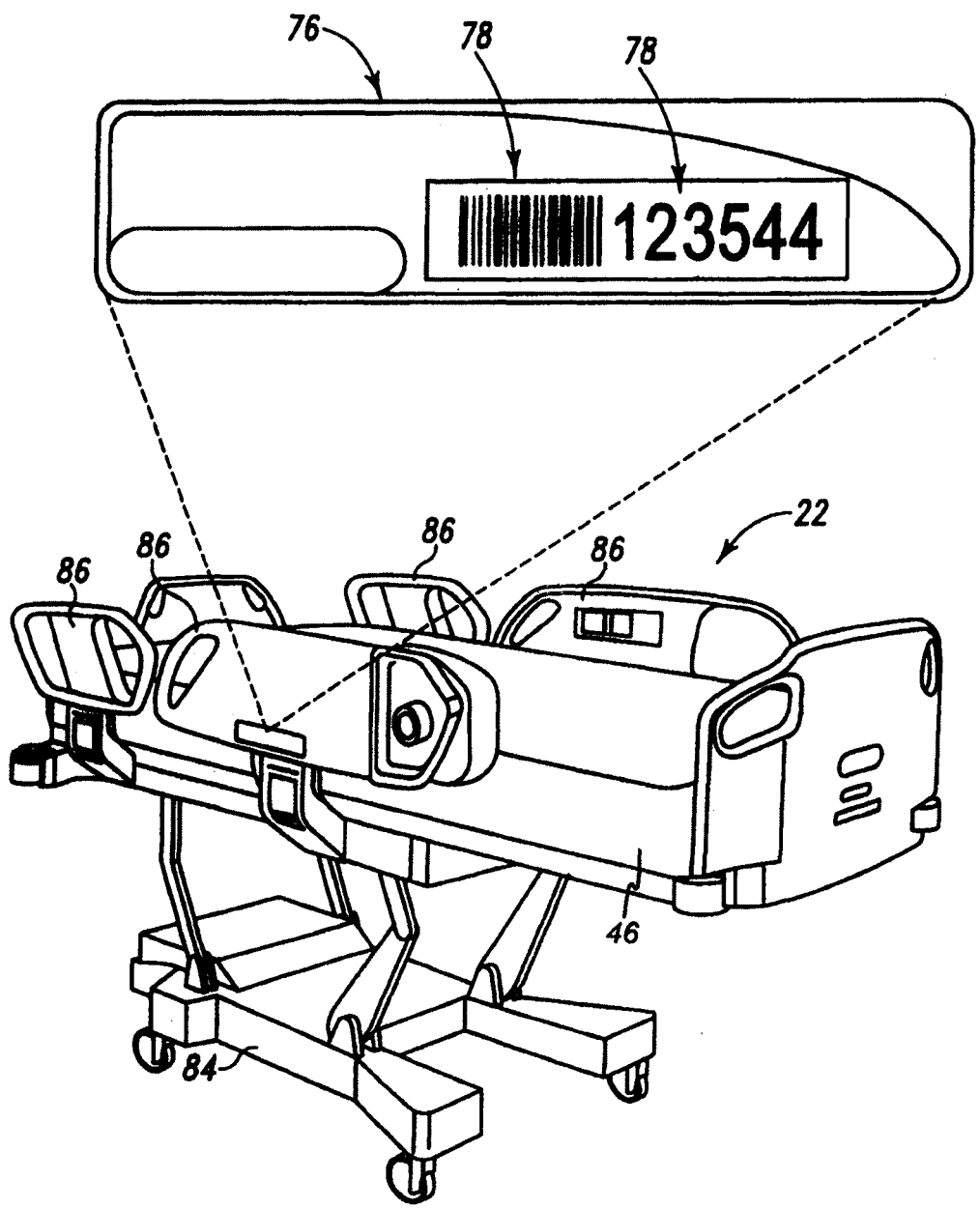

Referring now to FIGS. 3A and 3B (referred to collectively herein as FIG. 3), another embodiment of a hospital bed 22 is shown which includes a Care Alerts enabled indicator 80 and an on-line status indicator 82 on a base frame 84 of the bed 22. An enable button (not shown) is provided on one or more of siderails 86 of bed 22. Other than the fact that indicators 80, 82 are mounted to base frame 84 of the hospital bed 22 shown in FIG. 3, whereas corresponding indicators 71, 74 are mounted to siderail 52 of the hospital bed 22 shown in FIG. 2, indicators 80, 82 are substantially the same as indicators 71, 74 and therefore, the discussion above of indicators 71, 74 is equally applicable to indicators 80, 82. Optionally, the hospital bed 22 of FIG. 3 may also include a housekeeping button, with or without an associated housekeeping indicator, on one siderails 86 which functions in the same manner as button 72 (and indicator 73, if present) described above. The hospital bed 22 also has a label 76 with bed ID data 78 thereon. The bed ID data 78 includes numerical data and a bar code in the illustrative example of label 76. The label 76 of FIG. 3 is substantially the same as the label 76 of FIG. 2 so the same reference numeral is used. In some embodiments, the bed ID data 78 is the MAC address assigned to the network interface 340 of the hospital bed 22.

Figure 4:
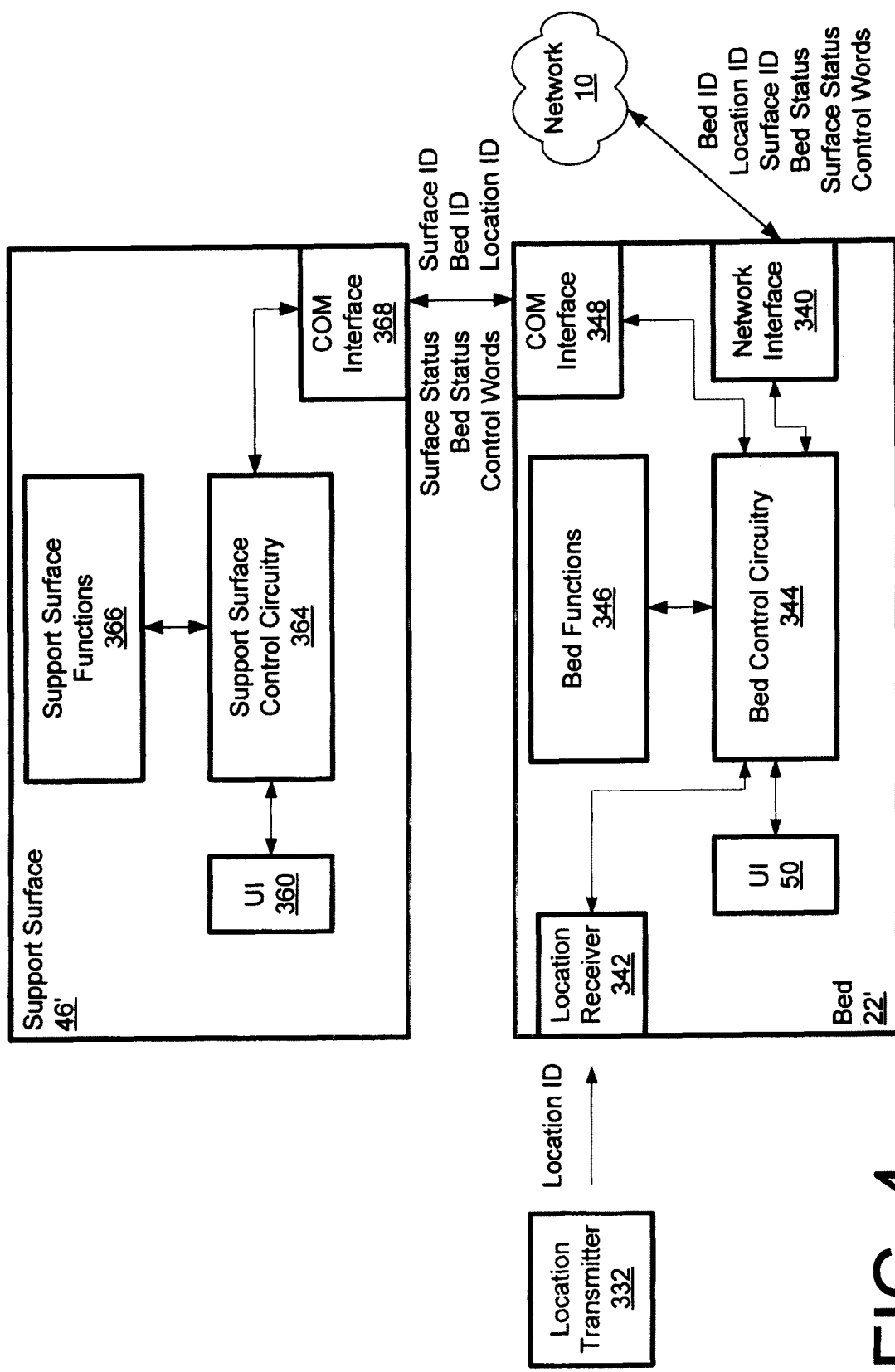
FIG. 4 is a block diagram showing electrical and control aspects of a bed and an associated support surface which communicate with a network of the healthcare facility via a network interface of the bed.
Figure 5:
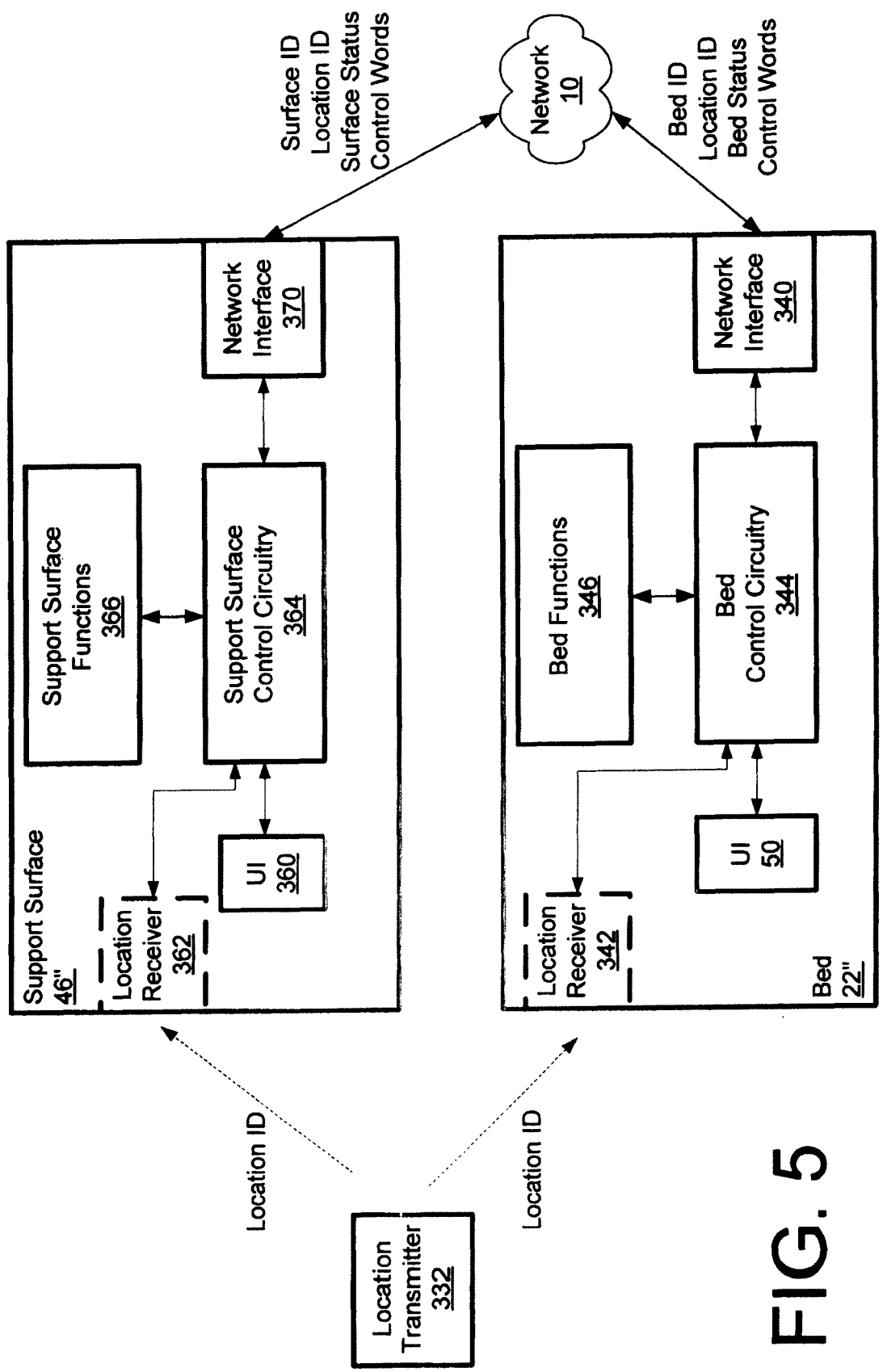
FIG. 5 is a block diagram showing electrical and control aspects of a bed and an associated support surface which each have a network interface for communicating with a network of the healthcare facility.
Figure 6:
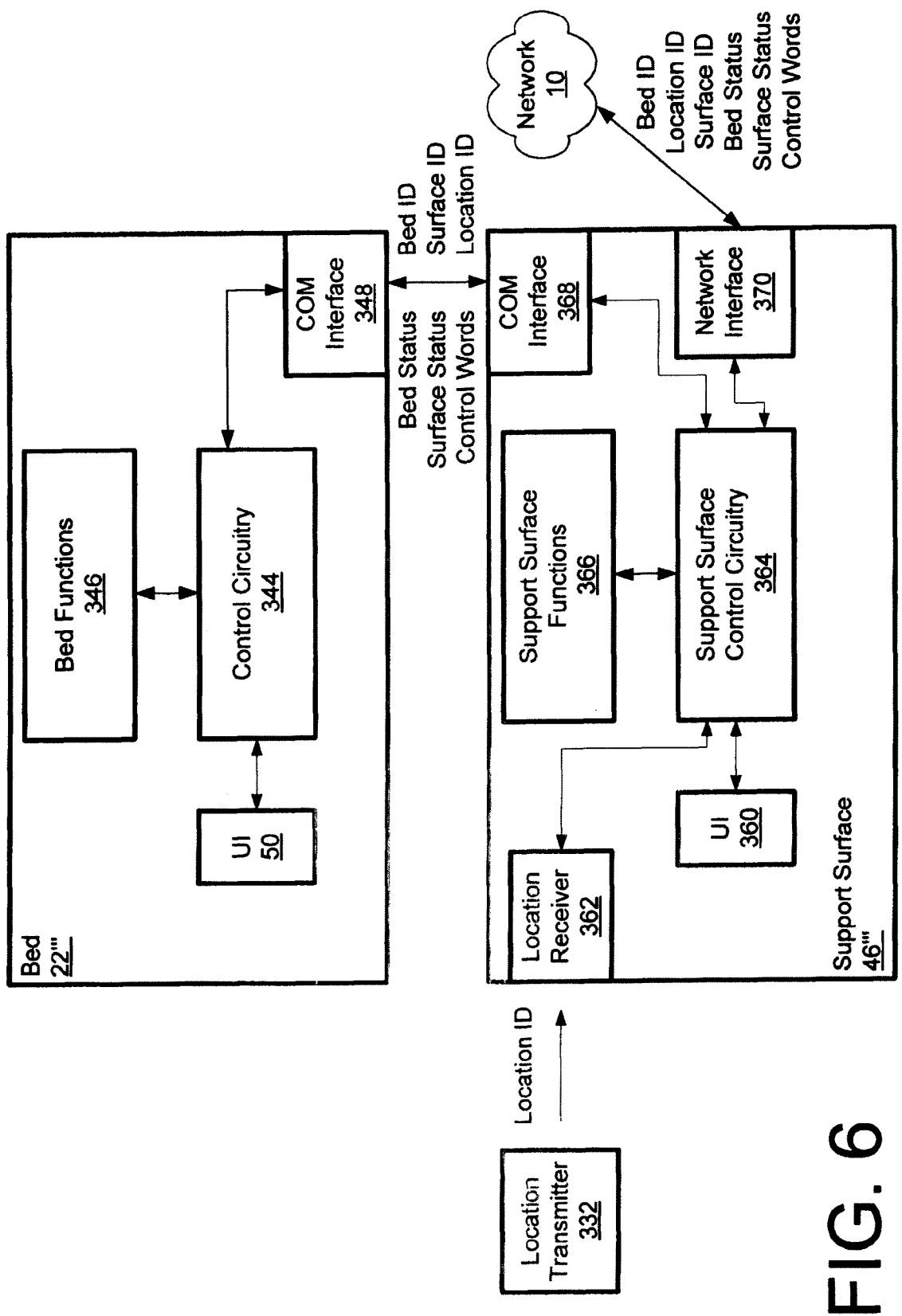
FIG. 6 is a block diagram showing electrical and control aspects of a bed and an associated support surface which communicate with a network of the healthcare facility via a network interface of the support surface.

Referring now to FIGS. 4-6, three embodiments of control aspects of the beds 22 and their support surfaces 46 are shown. In order to distinguish between beds 22 and supports surfaces 46 of these three embodiments, the following description uses a single prime (') for the bed 22' and support surface 46' of FIG. 4, a double prime (") for the bed 22– and support surface 46" of FIG. 5, and a triple prime ("') for the bed 22''' and support surface 46''' of FIG. 6. However, the present disclosure generally drops the prime designations when referring to beds 22 and support surfaces 46 in a general sense.

As shown in FIG. 4, the bed 22' includes a location receiver 342 to receive a location ID from a location transmitter 332. In one embodiment, each bed station 24 (See, FIG. 1) includes a location transmitter 332. However, it should be appreciated that location transmitters 332 may be positioned at other locales throughout the hospital and are not limited to bed stations 24. Moreover, it should be appreciated that a healthcare facility may chose to position location transmitters 332 at locales other than bed stations 24 thus resulting in some or all of the bed stations 24 without location transmitters 332.

The location transmitter 332 transmits a location identifier (ID) signal from which the location of the transmitter 332 may be determined. In one embodiment, the location transmitter 332 transmits a number such as, for example, a serial number which the has been uniquely assigned to the location transmitter 332. In such an embodiment, a user or technician may supply a surface association service of a computing device 4 with the location and location IDs for each location transmitter 332. As such, the surface association computing device 4 may maintain associations or mappings of location IDs to locations in the healthcare facility.

In another embodiment, the location transmitter 332 may be assigned a location ID that comprises data in addition to or instead of a serial number or an otherwise unique number. In particular, a location transmitter 332 may be assigned a location ID that comprises information regarding the location of the location transmitter 332. For example, the location ID may comprise one or more identifying location fields such as a floor, a room, a care unit, a zone, bed station, and/or some other location field. A technician or user may configure the location transmitters 332 with appropriate values for such fields thus resulting in a location ID for the location transmitter 332 from which the location of the location transmitter 332 may be determined. For example, a transmitter 332 may be configured to transmit an location ID with a value of "520" in the room field and a value of "2" in the zone field to indicate the transmitter 332 is located in zone 2 of room 520. It should be appreciated that the location ID may be implemented with numerous different fields, and the selection of appropriate fields for the location ID is influenced by the healthcare facility. For example, if the healthcare facility has unique room numbers for every room in the healthcare facility, then a room field is sufficient to uniquely identify the room in which the transmitter 332 is located. In contrast, for other healthcare facilities a room number may be insufficient and additional information (e.g. building number, wing, etc.) may be provided in order to uniquely specify the locations of the location transmitter 332 is located. Accordingly, the location ID of transmitter 332 is programmed at the discretion of the end users in some embodiments.

In one embodiment, the location transmitters 332 comprise stand-alone units that are not operatively coupled to the network 10 of the healthcare facility. Such an embodiment enables location transmitters 332 to be placed throughout a healthcare facility regardless of whether the healthcare facility has network infrastructure in the vicinity of a particular location transmitter 332. In other embodiments, one of more of the location transmitters 332 may be coupled to the network 10. In such an embodiment, a location identifier may be assigned to each location transmitters 332 via the network 10. In some embodiments, stand-alone transmitters 332 are battery powered, whereas network connected transmitters 332 receive power from the network (e.g. power of LAN). However, it should be appreciated that other means of powering the transmitters 332 are contemplated such as connecting to the main power of the healthcare facility.

Furthermore, various wireless technologies may be used to implement the location transmitters 332. In some embodiments, the location transmitters 332 transmit the location IDs using infrared signals. In other embodiments, the location transmitters 332 transmit the location IDs using radio frequency (RF) signals. Similarly, various wireless technologies may be used to implement the location ID receivers 342. Moreover, the location receivers 342 and location transmitters 332 may support multiple wireless technologies to increase the compatibility of the receivers 342 of the beds 22' with the transmitters 332. In other words, the receivers 342 may be implemented to receive multiple types of location signals thus supporting reception of location signals from different types of location transmitters 332. Similarly, the location transmitters 332 may be implemented to transmit multiple types of location signals thus supporting transmission of location IDs to different types of locations receivers 342.

The bed 22' includes a user interface 50 coupled to bed control circuitry 344 to enable a user such as a patient or a caregiver to control the operation of various functions 346 of the bed 22' as shown diagrammatically in FIG. 4. As mentioned above, the user interface 50 may comprise various user inputs (e.g. buttons, switches, touch sensitive displays) and various user outputs (e.g. LEDs, LCD displays, speakers) incorporated into siderails, footboards, headboards, handheld remotes or pendants of the bed 22'. Besides controlling bed functions 346 based upon input received from the user interface 50, the bed control circuitry 344 may further control bed functions 346 based upon data received via the network interface 340 and/or communication interface 348.

The support surface 46' includes a user interface 360 coupled to surface control circuitry 364 to enable a user such as a patient or a caregiver to control the operation of various functions 366 of the support surface 46' as shown in FIG. 4. Similar to the user interface 50 of the bed 22', the user interface 360 of the support surface may comprise various user inputs (e.g. buttons, switches, touch sensitive displays) and various user outputs (e.g. LEDs, LCD displays, speakers) incorporated into head section, foot section, and/or handheld remotes or pendants of the support surface 46'. Besides controlling support surface functions 356 based upon input received from the user interface 360, the surface control circuitry 364 may further control support surface functions 366 based upon data received from the bed 22' via communication interface 368. It should be appreciated that the bed 22' may transmit control data to the support surface 46' via the communication interfaces 348, 368 and such control data may be based upon data received from the bed user interface 50, location receiver 342, and/or network interface 340. Thus, the operation of the support surface 46' may be influenced by input received from the user interfaces 50, 360, location receiver 342, and/or the network interface 340.

In one embodiment, the communication interfaces 348, 368 are coupled to one another via a cable to establish a physical communications link between the bed 22' and the support surface 46'. In another embodiment, the communication interfaces 348, 368 comprise electrical contacts, interconnection ports, or the like which when the support surface 46' is positioned upon bed 22' results in the electrical contacts, interconnection ports or the like to engage each other to establish a physical communications link between the bed 22' and the support surface 46'. In yet another embodiment, the communication interface 348, 368 establish a wireless communications link between the bed 22' and the support surface 46'. Such a wireless communications link may be implemented using various wireless technologies such as infrared transceivers and/or RF transceivers. Moreover, the communication interfaces 348, 368 may support wirelessly communicating between the bed 22' and the support surface 46' via a capacitive and/or inductive coupling established between the communication interfaces 348, 368.

The network interface 340 of the bed 22' provides a wired and/or wireless communications link to the network 10 of a healthcare facility. The bed control circuitry 344 may monitor the bed functions 346 and maintain status data regarding the bed 22' and its support surface 46'. Using the network interface 340, the bed control circuitry 344 may communicate a location ID received via location receiver 342, bed status data of the bed functions 446 and/or surface status data of the surface 46' to the network 10 and the computing devices 4 coupled thereto. In one embodiment, the network interface 340 may be incorporated into the bed control circuitry 344. In another embodiment, the network interface 340 is provided by a separate networking card, wireless communications module (WCM), and/or a network interface unit (NIU).

In one embodiment, the network interface 340 transmits data between the bed 22' and the network 10 using a networking protocol such as, for example, the IEEE 802.11 (Wi-Fi) wireless communication protocols and/or the IEEE 802.3 (Ethernet) protocol. In an embodiment supporting a wired connection to the network 10, the network interface 340 includes a communications port to which a networking cable such as, for example, a coaxial cable, a twisted pair cable, or and fibre optic cable may be coupled in order to establish a wired communication link between the bed 22' and the network 10. In one embodiment, the communications port comprises an RJ-45 port, but other ports such as BNC connector ports are contemplated. In some wireless embodiments, the network interface 340 comprises a wireless transceiver to transfer data in accordance with the wireless protocol such as IEEE 802.11a, 802.11b, 802.11g, and/or 802.11n.

FIG. 5 shows an embodiment of control aspects of the bed 22" and support surfaces 46". The embodiment of FIG. 5 is similar to the embodiment of FIG. 4. Accordingly, similar components have been labeled with the same reference numerals in FIG. 4 and FIG. 5. As shown, support surface 46" of FIG. 5 differs from the embodiment of FIG. 4 in that the support surface 46' may further include a location receiver 362 and a network interface 370. The location receiver 362 receives a location ID signal comprising location ID data from a location transmitter 332 and provides the received location ID data to the support surface control circuitry 364. The location receiver 362 may be implemented in the manner described above in regard to the location receiver 342 of the bed 22".

The network interface 370 of the support surface 46" couples the support surface 46" to the network 10 of the healthcare facility. The network interface 370 may support establishing a wired and/or wireless communications link between the support surface 46" and the network 10. As shown, the support surface control circuitry 364 may use the network interface 370 to transfer support surface ID data, location ID data, support surface support data, control words and possibly other data between the network 10 and the support surface 46". Further, the network interface 370 may be implemented in a similar fashion to the network interface 340 of bed 22" which was described above in regard to FIG. 4.

Thus, the control circuitry 344, 364 of the bed 22" and the support surface 46" may respectively control the operation of bed functions 346 and support surface functions 366 based upon inputs received via the user interfaces 50, 360. Furthermore, the control circuitry 344, 364 may respectively control the operation of the bed functions 346 and support surface functions 366 based upon control words from the network 10 via the network interface 340, 370. Moreover, the bed 22" may receive information from the support surface 46" such as support surface ID data, location ID data, support surface status data, and control via network interfaces 340, 370. Likewise, the support surface may receive information from the bed 22" such as bed ID data, location ID data, bed status data, and control words via network interfaces 340, 370. While not shown, the bed 22" and support surface 46" may optionally comprise communication interfaces similar to the communication interfaces 348, 368 of FIG. 4 in order to transfer information such as support surface ID data, bed ID data, location ID data, support surface status data, bed status data, and control words between the bed 22" and support surface 46" without relying upon the network interfaces 340, 370.

Referring now to FIG. 6, an embodiment of control aspects of bed 22'" and support surface 46'" is shown. The embodiment of FIG. 6 is similar to the embodiments of FIGS. 4 and 5. Accordingly, similar components of FIG. 6 have been labeled with the similar reference numerals as corresponding components of FIG. 4 and FIG. 5. The embodiment of FIG. 6 basically reverses the roles of the bed 22' and support surface 46' of the embodiment of FIG. 4. In particular, whereas the bed 22' of FIG. 4 includes a location receiver 342 and a network interface 340 and the support surface 46' of FIG. 4 does not, the support surface 46'" of FIG. 6 includes a location receiver 362 and a network interface 370 and the bed 22'" of FIG. 6 does not.

Thus, the control circuitry 344, 364 of the bed 22'" and the support surface 46'" may respectively control the operation of bed functions 346 and support surface functions 366 based upon inputs received via the user interfaces 50, 360. Furthermore, the support surface control circuitry 364 may control the operation of the support surface functions 366 based upon control words from the network 10 via the network interface 370. Moreover, the bed 22'" and support surface 46'" may use communication interfaces 348, 368 in order to transfer information such as support surface ID data, bed ID data, location ID data, support surface status data, bed status data, and control words between the bed 22'" and support surface 46'". Further, it should be appreciated that operation of the bed 22'" may be controlled via the network 10 by transferring a control word to the network interface 370 of the support surface 46'" associated with the bed 22'". The support surface control circuitry 364 may in turn transfer the control word to the bed 22'" via the communication interfaces 348, 368.

In some embodiments, location receivers 342, 362 may be omitted from the beds 22 and/or the surfaces 46 of FIGS. 4-6. In such embodiments, the beds 22 and/or the surfaces 46 may obtain a location ID via several different techniques. For example, a caregiver may enter or select a location using the user interface 346 of the beds 22 and/or the user interface 360 of the surfaces 46.

As another technique, the beds 22 and/or surfaces 46 may obtain a location ID from a computing device 4 of the healthcare facility which determines the location of the beds 22 and/or surfaces 46 based upon network parameters associated with the beds 22 and/or surfaces 46 and provides the beds 22 and/or surfaces 46 with the appropriate location ID via network interfaces 348 and/or 368. In particular, the strength of signals or lack of signals between an access point 12 and beds 22 and/or surfaces 46 of the healthcare facility may be indicative of the position of such beds 22 and/or surfaces 46 in relation to the access point 12. Based upon data received from the beds 22, surfaces 46 and/or access points 12 regarding the strength of such signals or lack of such signals, the computer device 4 may determine the position of the beds and/or surfaces 46 in the healthcare facility using triangulation and/or other positioning techniques. The computer device 4 may also determine location of the bed 22" and/or surface 46 based upon other network parameters of the bed 22" and/or surface 46" such as network routing paths of communications between the bed/surface and the computing device 4.

Figure 10:
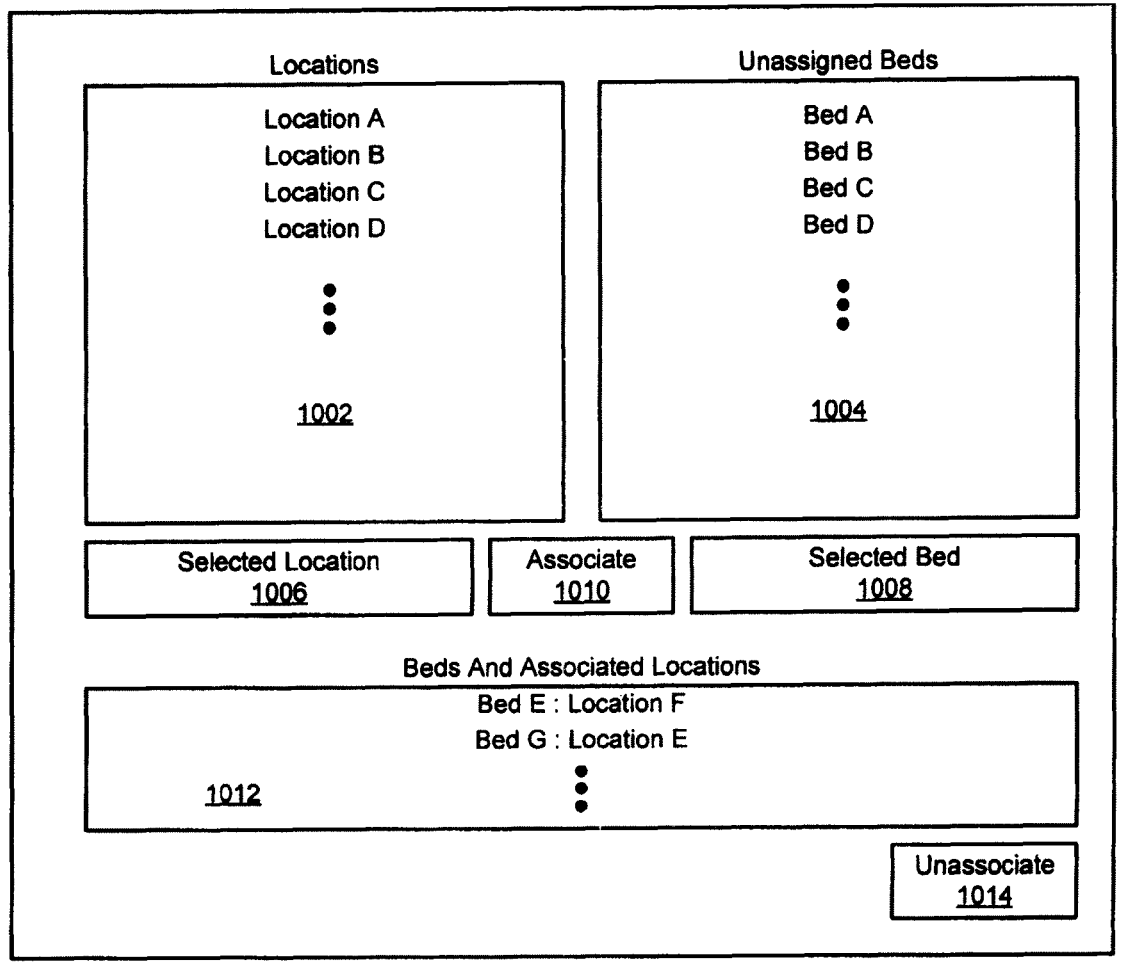
FIG. 10 is a block diagram of an interface via which a user may associate a bed with a location of the healthcare facility.
Figure 11:
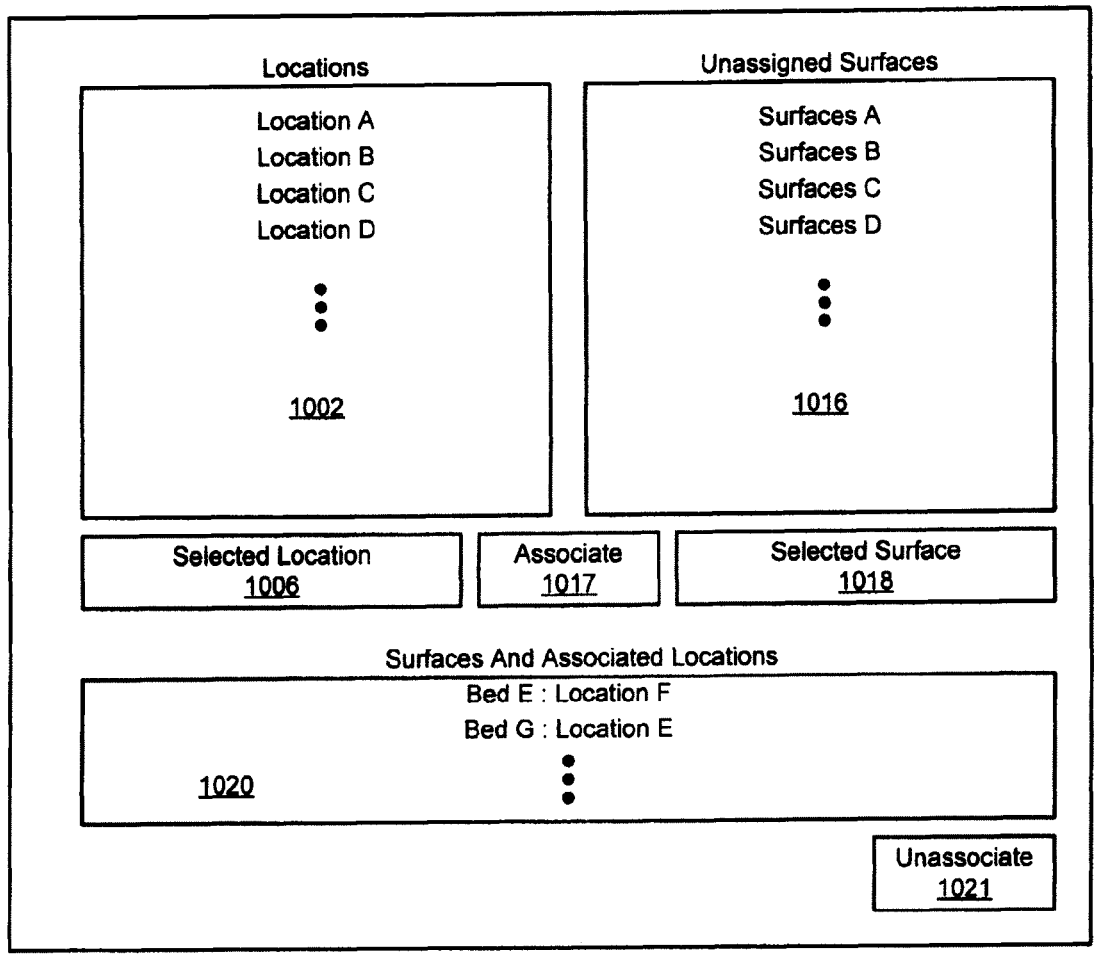
FIG. 11 is a block diagram of an interface via which a user may associate a surface with a location of the healthcare facility.
Figure 12:
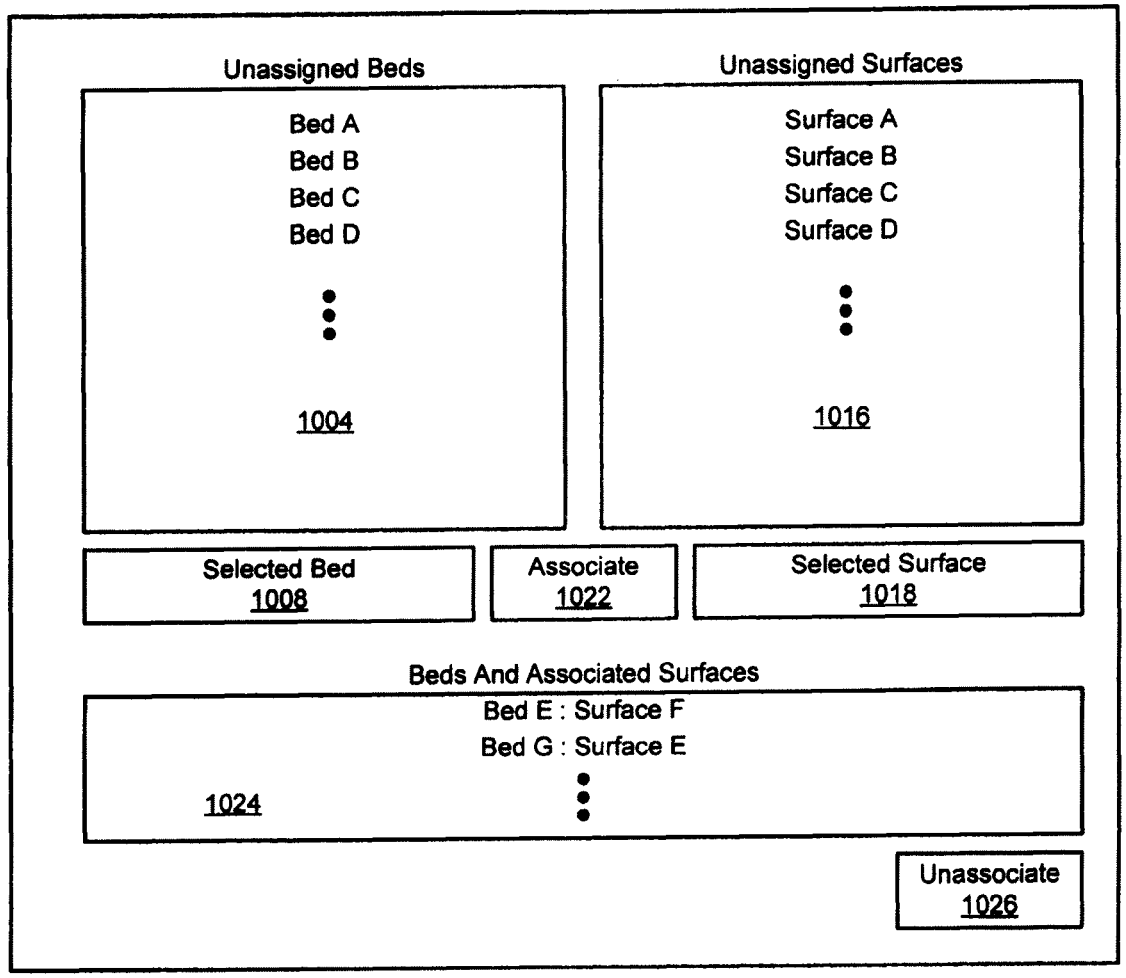
FIG. 12 is a block diagram of an interface via which a user may associate a bed and surface of the healthcare facility.
Figure 13:
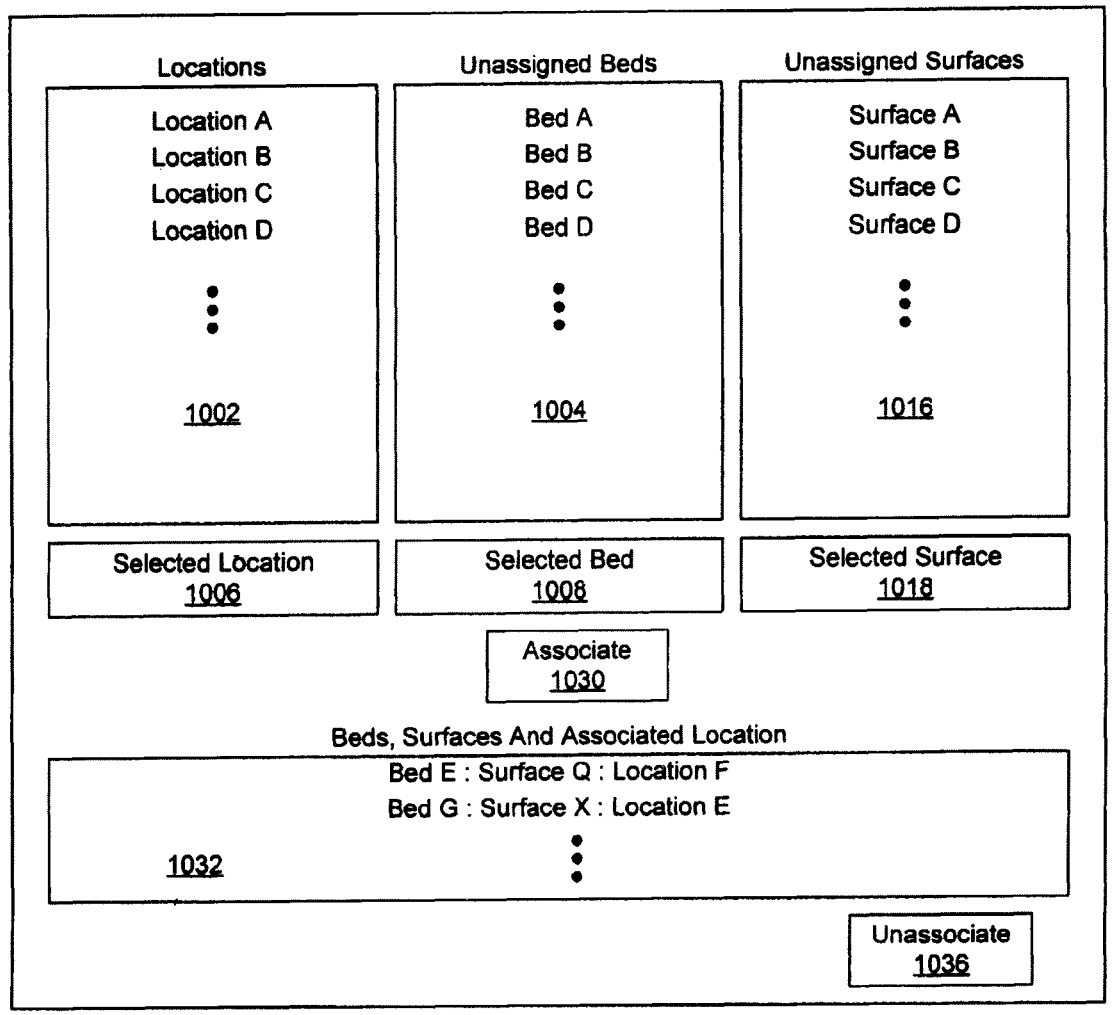
FIG. 13 is a block diagram of an interface via which a user may associate a bed, surface and a location of the healthcare facility.

As yet another technique for providing beds 22 and/or surfaces 46 with a location ID, an administrator may associate beds 22 and/or the surfaces 46 with locations using an interface of a computing device 4, the beds 22, and/or surfaces 46 such as the interfaces shown in FIGS. 10-13. FIG. 10 shows a user interface that enables an administrator to associate a bed 22 with a location. Similarly, FIG. 11 shows a user interface that enables an administrator to associate a surface 46 with a location. In such embodiments, the surface 46 may obtain the location ID from bed 22 and/or computing device 4, and the bed 22 may obtain the location ID from surface 46 and/or computing device 4. FIG. 12 shows a user interface that enables an administrator to associate a bed 22 and a surface 46, and FIG. 13 shows a user interface that enables an administrator to associate a location, bed 22 and a surface 46.

Referring now to the interface shown in FIG. 10 in more detail, the interface includes a locations control 1002 that identifies locations of the healthcare facility to which a bed 22 may be associated. The locations control 1002 may comprise a simple list control that provides a list of location identifiers that identify various locations of the healthcare facility to which a bed 22 may be associated. However, the locations control 1002 may comprise other types of user interface controls such as a tree control that provides a user with locations in a hierarchal manner. For example, the tree control may present location identifiers for units of the healthcare facility such as, for example, recovery, operating, and intensive care units. Under each of these units, the tree control may further present location identifiers such as room numbers or other subunits of the unit in question. These subunits may be even further divided by the tree control and so on.

The interface further includes an unassigned beds control 1004 that identifies beds 22 of the healthcare facility that have yet to be associated with a location of the healthcare facility. The unassigned beds control 1004 may be implemented in a manner similar to the locations control 1002. In particular, the unassigned beds control 1004 may comprise a simple list control that provides a list of bed identifiers which each identify a bed 22 of the healthcare facility that has yet to be associated with a location of the healthcare facility. In another embodiment, the unassigned beds control 1004 comprises a table control in which each row of the table corresponds to an unassigned bed of the healthcare facility and the columns provide information that identifies the respective bed such as, for example, serial number, MAC address, IP address, bed identifier, etc.

The interface of FIG. 10 further includes a selected location control 1006 and a selected bed control 1008. The selected location control 1006 displays the location identifier of the location selected from the locations control 1002. Similarly, the selected bed control 1008 displays the bed identifier 22 of the bed selected from the unassigned beds control 1004. The user interface also includes an associate control 1010. The associate control 1010 may include a button control or other control which when clicked, pressed, or otherwise activated causes the computing device 4 to associate the bed identified by the selected bed control 1008 with the location identified by the selected location control 1006. In another embodiment, the controls 1006 and/or 1008 are omitted. In such an embodiment, the interface may depict the selected location and/or bed by highlighting the appropriate identifier of the controls 1002, 1004. Accordingly, the associate control 1010 upon being activated may associate the bed highlighted or otherwise identified by the unassigned beds control 1004 with the location highlighted or otherwise identified by the locations control 1002.

As shown in FIG. 10, the user interface also include a beds and associated locations control 1012. The beds and associated locations control 1012 may be implemented in a manner similar to the beds control 1004. In particular, the beds and associated locations control 1012 may comprise a simple list control that provides a list bed identifiers and their associated location identifiers. In another embodiment, the beds and associated locations control 1012 may include a table control in which each row of the table corresponds to a bed and its associated location and the columns provide information regarding the bed and its associated location such as, for example, serial number, MAC address, IP address, bed identifier, and location identifiers (e.g. unit identifiers, subunit identifiers, etc.)

The user interface also includes an unassociate control 1014. The unassociate control 1014 may include a button control or other control which when clicked, pressed, or otherwise activated causes the computing device 4 to unassociate the bed or beds selected by the beds and associated locations control 1012 from their respective locations. In particular, the beds and associated location control 1012 may enable a user to select one or more beds, and the unassociate control 1014 upon being activated may unassociate the selected beds from their respective locations.

The user interface of FIG. 11 is similar to the user interface of FIG. 10 but associates surfaces 46 and locations of the healthcare facility instead of beds and locations of the healthcare facility. To this end, the user interface of FIG. 11 includes an unassigned surfaces control 1016 which presents a list of surface identifiers in a manner similar to the list of bed identifiers presented by the unassigned beds control 1004. Furthermore, the selected surface control 1028 presents the surface identifier selected via the unassigned surfaces control 1014 and the associate control 1017 upon being activated associates the surface 46 identified by the selected surface control 1018 and the location identified by the selected location control 1006. Moreover, the interface of FIG. 11 includes a surfaces and associated locations control 1020 that may be implemented in a manner similar to the beds and associated locations control 1012 in order to show surfaces and associated locations. The unassociate control 1021 upon being activated may unassociate surface(s) 46 and locations selected by the surfaces and associated locations control 1020.

The interface of FIG. 12 enables an administrator to associated beds 22 and surfaces 46. The unassigned beds control 1004, unassigned surfaces control 1016, selected beds control 1008 and selected surfaces control 1018 may be implemented in a manner similar to corresponding controls depicted in FIGS. 10 and 11. The associate control 1022 upon being activated may associate a bed 22 and surface 46 selected by the unassigned beds control 1004 and the unassigned surfaces control 1016. In turn, the beds and associated surfaces control 1024 may list beds 22 and associated surfaces 46 in a manner similar to the controls 1012, 1020 of FIGS. 10 and 11. The unassociate control 1026 upon being activated may unassociate beds 22 and surfaces 46 selected via the beds and associated surfaces control 1024.

Referring now to FIG. 13, the shown interface may be used by an administrator to associate a location, bed 22 and surface 46. The majority of the controls operate in a manner similar to such controls shown in FIGS. 10-12 and are thus referenced with the same numerals and not described here further. The associate control 1030 upon being activated associates the location, bed 22 and surface 46 selected by the controls 1002, 1004 and 1016 and shown by the controls 1006, 1008 and 1018. The beds and associated surfaces and locations control 1032 lists beds 22 of the healthcare facility that have been associated with a location and surface 46 in a manner similar to the controls 1012, 1020 and 1024 of FIGS. 10-12. Moreover, the beds and associated surfaces and locations control 1032 shows information regarding the associated beds, surfaces and locations to aid the administrator in determine which beds, surfaces and locations have been associated with one another. The unassociate control 1036 upon being activated may unassociated the beds 22, surfaces 46 and locations selected by the beds and associated surfaces and locations control 1032.

In one embodiment, data transmitted by the network interface 340 between the bed 22 and the network 10 includes bed status data as well as surface status data. One example of bed status data and surface status data is given in Tables 1-3 which are described below.

TABLE 1

| | 0x04 Bed Status Messages | 0x04 Location Byte | Bit | Name | ID | Read—R Write—W Auto Broadcast—B | Description |
|---|---|---|---|---|---|---|---|
| Standard | Standard Template | | | | | | |
| Bed Status | Brake Status | 1 | 4 | BedStatus | 0x04 | B | 1 = Brake set, 0 = Brake not set |
| | Surface prevent mode | 1 | 2 | BedStatus | 0x04 | B | 0 = Not activated, 1 = Activated |
| | Fall Prevention | | | | | | |
| | Bed Exit Armed | 1 | 1 | BedStatus | 0x04 | B | 0 = Armed, 1 = Not armed |
| | Bed Low Position | 1 | 3 | BedStatus | 0x04 | B | 0 = Bed not down, 1 = Bed down |
| | Head Rail Positions | 1 | 6 | BedStatus | 0x04 | B | 0 = Not down, 1 = Down |
| | Restraints | | | | | | |
| | Head rail positions | 1 | 6 | BedStatus | 0x04 | B | 0 = Not down, 1 = Down |
| | Foot rail positions | 1 | 5 | BedStatus | 0x04 | B | 0 = Not down, 1 = Down |

As shown in Table 1, brake status data indicates whether a brake for one or more of the casters of the hospital bed is set or not set; surface prevent mode data indicates whether a surface of the hospital bed is or is not activated to control air bladder pressures in a manner which attempts to inhibit formation of pressure ulcers (e.g., bed sores); bed exit armed status to indicate whether or not bed exit system which detects whether or not a patient has exited the bed is armed or not armed; bed low position data to indicate whether or not an upper frame which carries a mattress support deck is in its lowest position relative to a base frame of the bed; head rail position data to indicate whether head end siderails are up or down; and foot rail position data to indicate whether foot end siderails are up or down.

TABLE 2

| | | | | | | | |
|---|---|---|---|---|---|---|---|
| Enhanced | Enhanced Fall Prevention | | | | | | |
| Bed Status | PPM mode - Move | 3 | 8 | BedStatus | 0x04 | B | 0 = Not selected, 1 = Mode selected |
| | PPM mode - Start egress | 3 | 7 | BedStatus | 0x04 | B | 0 = Not selected, 1 = Mode selected |
| | PPM mode - Patient exit | 3 | 6 | BedStatus | 0x04 | B | 0 = Not selected, 1 = Mode selected |
| | PPM alarming | 3 | 5 | BedStatus | 0x04 | B | 0 = Not selected, 1 = Mode selected |
| | Enhanced Restraints | | | | | | |
| | Right head rail position | 2 | 1 | BedStatus | 0x04 | B | 0 = Not down, 1 = Down |
| | Left head rail position | 2 | 2 | BedStatus | 0x04 | B | 0 = Not down, 1 = Down |
| | Right foot rail position | 2 | 3 | BedStatus | 0x04 | B | 0 = Not down, 1 = Down |
| | Left foot rail position | 2 | 4 | BedStatus | 0x04 | B | 0 = Not down, 1 = Down |
| | Bed Safety | | | | | | |
| | Head Motor Lockout | 2 | 5 | BedStatus | 0x04 | B | 0 = Not locked, 1 = Locked |
| | Knee Motor Lockout | 2 | 6 | BedStatus | 0x04 | B | 0 = Not locked, 1 = Locked |
| | High-Low Motor Lockout | 2 | 8 | BedStatus | 0x04 | B | 0 = Not locked, 1 = Locked |
| | All Motor Lockout | 2 | 7 | BedStatus | 0x04 | B | 0 = Not locked, 1 = Locked |
| | Wound Prevention | | | | | | |
| | Surface turn assist left mode | 3 | 2 | BedStatus | 0x04 | B | 0 = Not active, 1 = Active |
| | Surface turn assist right mode | 3 | 3 | BedStatus | 0x04 | B | 0 = Not active, 1 = Active |
| | Surface max inflate mode | 3 | 4 | BedStatus | 0x04 | B | 0 = Not active, 1 = Active |
| | Heel suspension mode | 5 | 4 | BedStatus | 0x04 | B | 0 = Not active, 1 = Active |
| | Rotation mode | 5 | 3 | BedStatus | 0x04 | B | 0 = Not active, 1 = Active |
| | Optirest mode | 5 | 2 | BedStatus | 0x04 | B | 0 = Not active, 1 = Active |
| | Pulmonary | | | | | | |
| | Percussion | 4 | 5 | BedStatus | 0x04 | B | 0 = Not active, 1 = Active |
| | Vibration | 4 | 6 | BedStatus | 0x04 | B | 0 = Not active, 1 = Active |
| | Operational Alerts | | | | | | |
| | Housekeeping | 5 | 1 | BedStatus | 0x04 | B | 0 = Not active, 1 = Active (switch status, not bed cleaned status) |
| | Maintenance Alerts | | | | | | |
| | Battery status modes, 2 bits | 4 | 2 | BedStatus | 0x04 | B | 0 0 = No battery present |
| | | 4 | 3 | BedStatus | 0x04 | B | 0 1 = Battery disconnected |
| | | | | | | | 1 0 = Battery needs charging |
| | | | | | | | 1 1 = Battery fully charged |
| | AC power not present mode | 4 | 1 | BedStatus | 0x04 | B | 1 = AC present, 0 = AC not present |
| | Service required light | 4 | 4 | BedStatus | 0x04 | B | 0 = No service req'd, 1 = Service req'd |

TABLE 2-continued

| Other Bed Data | | | | | | |
|---|---|---|---|---|---|---|
| CPR mode | 3 | 1 | BedStatus | 0x04 | B | 0 = Not active, 1 = Active |
| AC power present mode | 4 | 1 | BedStatus | 0x04 | B | 1 = AC present, 0 = AC not present |
| Nurse Call switch | 4 | 7 | BedStatus | 0x04 | B | 0 = Not active, 1 = Active |
| CareAlert Switch | 4 | 8 | BedStatus | 0x04 | B | 0 = Not active, 1 = Active |

As shown in Table 2, patient position mode data indicates whether or not a patient position monitoring system of the hospital bed is in move mode in which patient movement of a first amount is considered an alarm condition, a start egress mode in which patient movement of a second amount greater than the first amount is considered an alarm condition, or patient exit mode in which patient movement of a third amount greater than the second amount (including movement off of the bed) is considered an alarm condition, and the patient position mode data also indicates whether or not an alarm condition, of the selected mode, has occurred. As also shown in Table 2, siderail position data indicates whether each of a right head rail, a left head rail, a right foot rail, and a left foot rail are in up or down positions; motor lockout data indicates whether or not a head motor which is operable to raise and lower a head section of the mattress support deck is locked out; whether or not a knee motor which is operable to raise and lower a thigh section (or seat section) of the mattress support deck is locked out; whether or not one or more high-low motors which are operable to raise and lower an upper frame carrying the mattress support deck relative to a base frame of the bed is locked out; and whether or not all of the motors just described are locked out.

Table 2 further shows surface status data such as whether or not a left turn assist mode or right turn assist mode to turn the patient, on a one-time basis, in one direction or another is active; whether or not a max inflate mode to inflate air bladders of the mattress to a preprogrammed maximum pressure to harden the surface for patient transfer, patient ingress or egress, or CPR is active; whether or not a heel suspension mode to deflate bladders in a heel region of the patient to attempt to inhibit formation of pressure ulcers on the patient's heels is active; whether or not a rotation mode to cyclically rotate the patient to the left and to the right is active; whether or not an optirest mode to sequentially inflate head zone bladders, seat zone bladders, and foot zone bladders is active; whether or not percussion to pulsate one or more air bladders of the surface is active; and whether or not vibration to vibrate one or more air bladders of the surface is active. In other embodiments, the surface status data may indicate whether or not a low air loss mode in which air is expelled from openings in the mattress to cool the patient and/or to transport moisture away from the patient is active and/or whether or not an alternating pressure mode in which sets of alternating bladders are each inflated and deflated at different times so that different portions of the patient are primarily supported by different bladders sets at different times is active.

As further shown in Table 2, housekeeping data indicates whether or not a housekeeping switch or button on the bed is active (e.g., has been pressed) to request that a staff member clean the hospital bed and/or the associated room; battery status data indicates whether or not a battery is present on the bed, whether or not the battery is disconnected from bed circuitry, whether or not the battery needs to be charged, and whether or not the battery is fully charged; AC power data indicates whether or not AC power is being received by the bed; service data indicates whether or not the bed needs to serviced; CPR mode data indicates whether or not a CPR release handle of the bed, which causes a head section of the mattress support deck to be lowered rapidly so that CPR can be quickly administered to a patient, has been activated; nurse call data indicates whether or not a nurse call switch to request to speak with a caregiver has been activated; and Care Alert data indicates whether or not a Care Alert switch to enable and disable any Care Alerts set up in templates at a remote computer has been activated.

TABLE 3

| | Object Dictionary Data | | | | | Description |
|---|---|---|---|---|---|---|
| Other | Bed Management | | | | | |
| | Bed Type | 0x02 record | BedType | 0x02 | B | Bed type byte, revision number |
| | Bed Location | 0x05 record | BedLocation | 0x05 | R | Wall ID, 4 bytes |
| | Pulmonary | | | | | |
| | Head Angle | OD entry 0x3262, 0x00 | Pulmonary | <3262000 | R | Object dictionary entry 16-bit unsigned (VC), 16-bit signed (TC) |
| | Switches | | | | | |
| | Installed Switches | OD entry 0x3642, 0x00 | ISwitches | <3642000 | R/W | Object dictionary entry |
| | | 1 | 4 | | | 1 = brake switch installed, 0 = not installed |
| | | 1 | 5 | | | 1 = siderail foot switches installed, 0 = not installed |
| | | 1 | 6 | | | 1 = siderail head switches installed, 0 = not installed |
| | | 1 | 7 | | | 1 = Nurse call switch input available, 0 = not available |
| | | 1 | 1 | | | 1 = Bed exit info available, 0 = not available |
| | | 1 | 3 | | | 1 = Bed down info available, 0 = not available |

TABLE 3-continued

| Object Dictionary Data | | | | | Description |
|---|---|---|---|---|---|
| Weight | | | | | |
| Patient Weight | OD entry | Weight | <2180000 | R | Data in Hex format. Convert to decimal divide by 10 to get weight in pounds. |

As shown in Table 3, bed type data indicates the type of bed (e.g., manufacturer and model number) transmitting the data; bed location data indicates the location in the healthcare facility at which the bed is located such as the location ID received from the location transmitters 332; head angle data indicates an angle at which the head section of the mattress support deck is elevated relative to another portion of the bed, such as an upper frame or another deck section, or relative to horizontal or vertical; switch installed data indicates whether or not one or more brake switches, siderail foot switches, siderail head switches, and/or nurse call switches are installed on the bed; information availability data to indicate whether or not bed exit data and/or bed low position data is available from the bed; and patient weight data indicates the weight of a patient as measured by a weigh scale system of the hospital bed.

Any of the bed status data in any of the three above tables may be transmitted to the network 10 via network interface 340 and/or network interface 370. The data may then used by one or more healthcare support services provided by the computing devices 4 such as a nurse call service which operates to contact assigned caregivers when certain conditions on the bed 22 or surface 46 are detected, a workflow service to assign tasks to caregivers and other staff members, a locating-and-tracking service to track the whereabouts of people and/or equipment, an admission discharge and transfer (ADT) service, a bed assignment service, a surface/bed association service and the like.

It will be appreciated that a hospital will have multiple beds, similar to bed 22, multiple support surfaces 46 associated with the various beds 22, and multiple location transmitters 332 positioned throughout the healthcare facility. Each location transmitter 332 may be mounted at a particular location in a hospital. For example, one or more location transmitters 332 may be located in various patient rooms such as, for example, at the bed stations 24. Each bed 22, support surface 46, and location transmitter 332 in one embodiment is assigned a unique identification (ID) code, such as a serial number. In some embodiments, one or more of the computing devices 4 comprises software to associate bed ID data with location ID data to keep track of which bed 22 is located in each room of the hospital and convey this information to caregivers. Moreover, one or more of the computing devices 4 comprises software to associated surface ID data with bed ID data to keep track of which support surface 46 is associated with which bed 22.

Beds 22 and surfaces 46 may each have power cords (not shown) that are plugged into electrical outlets in hospital rooms during normal use of the beds 22 regardless of whether the beds 22 communicate with other devices in the associated network via wired or wireless connections. In some embodiments, beds 22 may have a socket into which a power cord of an accessory such a surface 46 may be plugged. According to this disclosure, when the power cords of beds 22 and/or surfaces 46 are unplugged, which usually happens when the bed is to be moved from one location in a healthcare facility to another, the associated Care Alert templates are automatically disabled. Thus, even if the bed 22 and/or surface 46 is still able to communicate wirelessly during transit from one location to another, the associated nurse call system does not initiate any communications with the wireless communication devices carried by the caregivers. Such alarm notifications are not generally needed because other caregivers should be accompanying the bed 22 during transit. Before the automatic disabling of the Care Alert templates, a slight delay period, such as 10 or 20 seconds, may be required to elapse so that, if the bed's power plug was unplugged inadvertently, there is time to plug the bed back in before the Care Alert templates are disabled.

In the case of beds 22 and/or surfaces 46 that communicate wirelessly, data is sent from the respective wireless transmitters to notify the associated nurse call system that the bed and/or surface has been unplugged. Such data may be transmitted after the above-mentioned delay period (i.e., the bed determines when the delay period has elapsed) or substantially immediately in response to the bed and/or surface being unplugged (i.e., the nurse call system determines when the delay period has elapsed). In the latter case, appropriate data is sent from the wireless transmitter if the bed and/or surface is plugged back in before the delay period elapses so that the nurse call system does not disable the Care Alert template.

Beds and/or surfaces having wireless communication circuitry may be powered by battery back-up power or by one or more capacitors for a period of time sufficient to permit the transmission of data indicating that the bed and/or surface has been unplugged (and, in some embodiments, for a return acknowledgment to be received by the bed and/or surface). Additionally or alternatively, the nurse call system may also conclude that the bed 22 and/or surface 46 has been unplugged and is in transit if a different wireless transceiver or receiver receives a signal from the bed 22 and/or surface 46, such as a wireless access point or a transceiver of an associated locating-and-tracking system, and proceed to automatically disable the Care Alert alarm notifications as a result.

Moreover, it should be appreciated that even beds 22 without a network interface 340 or a network interface 340 without wireless circuitry may still notify the associated nurse call system that the bed 22 has been unplugged using its associated support surface 46 to relay such information. In particular, the bed 22 may inform the support surface 46 via communication interfaces 348, 368 that the bed 22 has been unplugged and the support surface 46 may in turn send such information to the network 10 using its network interface 370. Likewise, it should be appreciated that even surfaces 436 without a network interface 370 or a network interface 370 without wireless circuitry may still notify the associated nurse call system that the surface 46 has been unplugged using its associated bed 22 to relay such information. In particular, the support surface 46 may inform the bed 22 via communication interfaces 348, 368 that the support surface 46 has been unplugged and the bed 22 may in turn send such information to the network 10 using its network interface 340.

In some embodiments, after the bed 22 and/or surface 46 reaches its new location and the associated power cord is plugged back in, a caregiver signals the nurse call system to re-enable the Care Alert templates for the particular bed. Caregivers may re-enable the Care Alert templates for the particular bed 22 by making appropriate entries on either an audio station in the room, a computer at the master nurse call station, or the wireless communication device carried by the caregiver. The re-enabling of the Care Alert template may be made by voice commands entered into the wireless communication device in some embodiments.

Because the nurse call system receives bed ID data, the particular Care Alert template associated with the bed 22 is known by the nurse call system. Thus, unless overridden by users of the nurse call system, the association between bed, patient, and assigned caregivers is maintained by the nurse call system even if the bed is moved to a new location. If one of the assigned caregivers does not re-enable the Care Alert template within a predetermined period of time after the nurse call system determines that the bed has been plugged back in (such determination being made in any of the ways described above for determining that the bed has been unplugged), then a reminder to re-enable the Care Alert template may be initiated by the nurse call system to the wireless communication devices carried by one or more of the assigned caregivers.

In alternative embodiments, the nurse call system may re-enable the Care Alert templates automatically after bed 22 and/or surface 46 has been moved and then plugged back in. Alternatively or additionally, the nurse call system may initiate a communication to the wireless communication devices of one or more assigned caregivers advising that the nurse call system will re-enable the Care Alert templates within a predetermined period of time unless receiving instructions not to do so. Alternatively or additionally, the nurse call system may initiate a communication to the wireless communication devices of one or more assigned caregivers with a notification that an assigned bed is now determined to be at a new location and the one or more caregivers should communicate via appropriate measures (entries on a nurse call computer, voice commands, entries on a user interface of a wireless communication device, etc.) to re-enable the associated Care Alert templates.

The data received from beds 22 and/or support surface 46 by the associated nurse call system may be provided to other systems of the hospital network. In one example, beds 22 having weigh scale systems transmit patient weight to a nurse call system which, in turn, transmits the patient weight data to an electronic medical records (EMR) system which, in turn, stores the weight information in the associated patient's record. The nurse call system may convert the data from one communication protocol into another communication protocol. Thus, patient weight data received by the nurse call system may be converted by the system into the Health Level 7 (HL7) protocol for transmission to the EMR system. In some embodiments, patient weight data is transmitted to the nurse call system only in response to a query initiated by a caregiver via entries on a nurse call computer, voice commands, entries on a user interface of a wireless communication device, etc. Such a system reduces extraneous data transmissions on the network for data, such as patient weight, of the type which does not vary much with time and which may be desired by caregivers only sporadically.

Bed status data from beds 22 and surface status data from surfaces 46 may be routed to different computers or to different software applications on the same computer. For example, some bed status data packets may be sent by beds 22 and used by a nurse call software application and other bed status data packets may be sent by beds 22 and used by some other software application, such as a workflow software application. Each of the data packets of bed status data may include a destination address, such as an Internet Protocol (IP) address, of the computer for which the particular bed status data is destined. As previously mentioned different bed status data and/or surface status data may be destined for different software applications run on the same computer, in which case the IP address included in each packet of bed status data and/or surface status data may or may not have the same IP address depending upon whether or not the software applications on the same computer have been assigned different IP addresses. Alternatively or additionally, the bed status data and/or surface status data may be routed to different software application, be they on the same computer or different computers, based on the data type.

In addition, each of the data packets of bed status data include bed identification data, such as a serial number of the associated bed 22 and/or an IP address and/or a MAC address of the associated bed 22. Furthermore, if known, then each of the data packets of bed status data include location data, such as a room number or other location ID indicating the location of the associated bed 22 in the healthcare facility. In accordance with this disclosure, the IP address of each of beds 22 may be assigned in accordance with the Dynamic Host Configuration Protocol (DHCP). Likewise, each of the data packets of surface status data include surface identification data, such as a serial number of the associated surface 46 and/or an IP address and/or a MAC address of the surface 46. Furthermore, if known, then each of the data packets of surface status data include location data, such as a room number or other location ID indicating the location of the associated surface 46 in the healthcare facility. In accordance with this disclosure, the IP address of each of surfaces 46 may be assigned in accordance with the Dynamic Host Configuration Protocol (DHCP).

As mentioned above, one or more computing devices 4 may provide a surface association service that associates beds 22 and supports surfaces 46 to one another. Hospital beds 22 may support various makes and models of support surfaces 46. As explained in more detail below, a computing device 4 may send control messages to a bed 22 based upon the surface status data for the surface 46 of the bed 22 and/or bed status data of the bed 22. Similarly, a computing device 4 may send control messages to a support surface 46 based upon the surface status data for the surface 46 of the bed 22 and/or bed status data of the bed 22. The surface association service supports such activities by maintaining associations between beds 22 and the support surfaces 46 placed upon the decks 47 of the beds 22.

Figure 7:
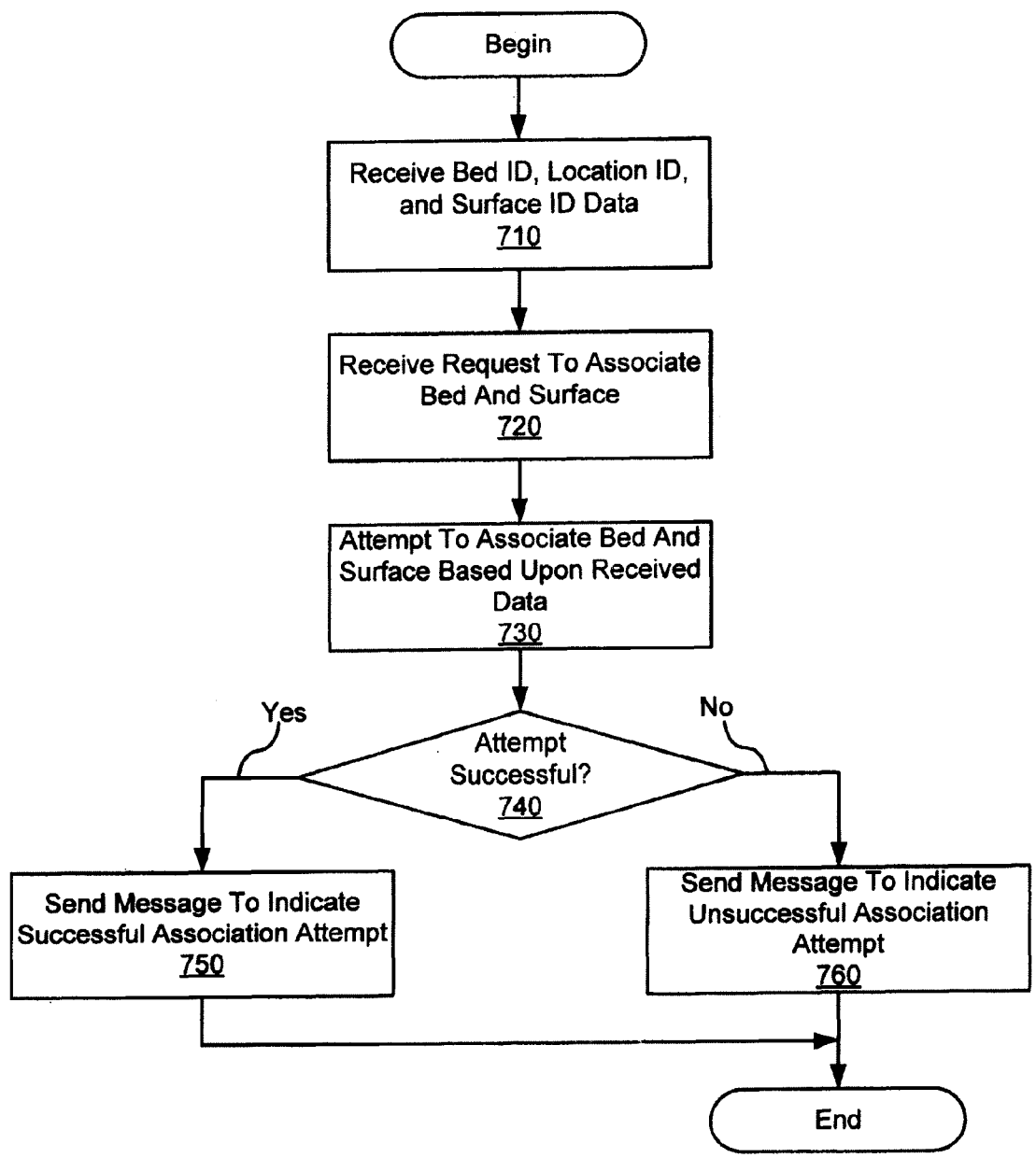
FIG. 7 is a flowchart of one embodiment of a support surface association method which may be implemented by a computing device of the healthcare facility in order to provide a support surface association service that associates beds and support surfaces of the healthcare facility to one another.

One embodiment of a surface association method implemented by a service association service of one or more computing devices 4 is shown in FIG. 7. As indicated at block 710, the computing device 4 may receive bed ID data and location ID data from beds 22 of the healthcare facility and may receive surface ID data and location ID data from support surfaces 46 of the healthcare facilities. It should be appreciated that the computing device 4 may receive such data regardless of whether the bed 22 and support surface 46 are implemented in accord with the embodiment shown in FIG. 4 or the embodiments shown in FIG. 5 or FIG. 6.

As indicated at block 720, the computing device may receive a request to associate a bed 22 and surface 46 with one another. In one embodiment, the computing device 4 may receive the surface association request in response to a caregiver activating one or more inputs of the user interface 50 of the bed 22 and/or the user interface 360 of the surface 46. In some embodiments, the user interfaces 50, 360 may include a button, switch and/or other user input that, in response to being activated, initiates the surface association request. In another embodiment, the computing device 4 further supports beds 22 and/or surfaces 46 which were designed without surface association requests in mind and therefore do not provide a button, switch an/or other user input for initiating a surface association request. In such an embodiment, the computing device 4 may detect a surface association request based upon bed status data and/or surface status data received from the bed 22 and/or surface 46 indicating the occurrence of a predetermined sequence of actions which the computing device 4 recognizes as a surface association request.

For example, the predetermined sequence of actions for a surface association request may be defined as toggling the brake release on a bed 22 a threshold number (e.g. 3) or more times within a predetermined period (e.g. 2 seconds). However, it should be appreciated that the computing device 4 may define and therefore recognize just about any sequences of actions as an association request. Such actions may involve actuating the user interface 50, 460 and/or actuating mechanical aspects (e.g. raising/lowering siderails, toggling brakes, etc.) that do not involve the user interfaces 50, 360. Generally, the computing device 4 assigns an event to be detected a sequence of actions that is unlikely to occur in the normal course of operation of the bed 22 and/or surface 46 in order to reduce the likelihood of false or inadvertent requests. However, it should also be appreciated that inadvertent requests are generally not problematic as such inadvertent requests merely result in extra processing by the computing device 4 and re-association of the bed 22 and surface 46.

Moreover, the sequence of actions assigned to an event do not necessarily need to be unique. In other words, the computing device 4 may assign different events to the same sequence of actions. For example, the computing device 4 may associate the same sequence of actions to association requests, device identifications as explained below in regard to FIG. 8, and/or confirmations as explained below in regard to FIG. 9. In such cases, the computing device 4 may determine an event has occurred in response to detecting a sequence of actions associated with multiple types of events. The computing device 4, in response to detecting the sequence of actions, may then determine the type of event based upon other information such as the context in which the sequence of actions was detected. For example, a user may unbrake and brake casters of a bed 22 in order to initiate a surface association request. The computing device may receive via a surface 46 data indicative of the unbrake and brake actions and may determine that the actions are a surface association request based upon there being no pending confirmations for the surface 46. The computing device may then request a user to confirm a bed 22 to associated with the surface 46. In response to the request, the user again may unbrake and brake casters of the same bed 22 in order to confirm the bed 22 as the bed to be associated with the surface 46. The computing device may again receive via the surface 46 data indicative of the unbrake and brake actions and may determine that the actions are a confirmation since the computing device is awaiting a confirmation in regard to the surface 46.

At block 730, the computing device 4 attempts to associate beds 22 and surfaces 46 based upon the data received from each bed 22 and surface 46. In an embodiment, the computing device 4 may determine that a bed 22' and surface 46' (See, FIG. 4) are associated based upon bed ID data and surface ID data received from the network interface 340 of the bed 22' since the computing device 4 is capable of determining that the bed ID data and surface ID data is received from a single source (e.g. bed 22"). Similarly, the computing device 4 may determine that a bed 22''' and surface 46''' (See, FIG. 6) are associated based upon bed ID data and surface ID data received from the network interface 370 of the surface 46''' since the computing device 4 is capable of determining that the bed ID data and surface ID data is received from a single source (e.g. surface 46").

For a bed 22" and surface 46" that each have a network interface (See, FIG. 5), the computing device 4 may associate the bed 22" and surface 46" based upon the location ID data received from their network interfaces 340, 370. In particular, the computing device 4 may associate the bed 22" with the surface 46" based upon their respective location ID data identifying the bed 22" and surface 46" as being in the same location.

In one embodiment, computing device 4 as indicated at block 730 may attempt to memorialize the determined association between the bed 22 and surface 46. For example, the computing device 4 may update a database to reflect the determined association between the bed 22 and surface 46. The computing device 4 in other embodiments may memorialize the determined association by updating data stored in memory of the computing device 4, requesting another computing device 4 to store the association between the bed 22 and surface 46, and/or storing the association in a non-volatile memory (e.g. hard drive, RAID drive, etc.) of the computing device 4.

As indicated at block 740, the computing device 4 may determine whether the attempted association was successful. The computing device 4 may be unable to associate a bed 22 and surface 46 for a number of reasons. For one, multiple beds 22 and/or surfaces 46 may be located sufficiently close to the same location transmitter 332 of the healthcare facility to result in the multiple beds 22 and/or surfaces 46 receiving the same location ID data. Thus, the computing device 4 in such circumstances may be unable to uniquely associate a single bed 22 with a single support surface 46 without further data to distinguish the multiple beds 22 and/or surfaces 46. However, it should also be appreciated that by careful positioning of the location transmitters 332 and tuning of the transfer range between the location transmitters 332 and location receivers 342, 362, the number of conflicts may be reduced to a very small number and/or practically eliminated for a given healthcare facility. As another example, the computing device 4 may experience one or more faults and/or errors such as, for example, disk read errors, network faults, database timeouts, etc. which prevent the computing device 4 from completing the requested association.

If the requested association was successful, the computing device 4 as indicated at 750 may provide the person requesting the association with an indication of the successful association. In one embodiment, the computing device 4 transmits a control message to the bed 22 and/or surface 46 which results in the user interface 50 of the bed 22 and/or the user interface 360 of the surface 46 to display the successful association. For example, a user interface 50, 360 in response to the received control message may display a textual message upon its display and/or may update the status of one or more LEDs of the user interface 50, 360 (e.g. turning on, turning off, blinking, and/or changing the illuminated color of one or more LEDs) to signal the success of the requested bed/surface association. Alternatively, or in addition to, the computing device 4 may send a message (e.g. audio message and/or text message) to a pager, PDA or other type of wireless communication device such as Vocera® handsets or telephone handsets that have bidirectional voice communication capability and that may have text messaging capability of a caregiver located near the bed 22 and surface 46 and/or an audio message to an audio station and/or text message of the bed station 24 near the location identified by the received location ID data.

Conversely, if the requested association was not successful, the computing device may provide the person requesting the association with an indication of the unsuccessful association of the bed and surface in a manner similar to block 750 as indicated at block 760. In one embodiment, if the requested association was not successful due to multiple beds 22 and/or surfaces 46 being identified for a single association, the computing device 4 may alert a user of the computing device 4 and/or the person who requested the association of the bed 22 and the surface 46 of the conflict so that they can manually resolve the conflict. For example, the user requesting the association may simply manually enter the bed ID data and surface ID data into the computing device 4 and/or relay such data to an operator of the computing device 4 for entry into the computing device 4 or may be instructed to perform a function on the bed (e.g. raise then lower siderail, unbrake then brake casters, etc.) to indicate the bed to which a surface is to be associated.

Figure 8:
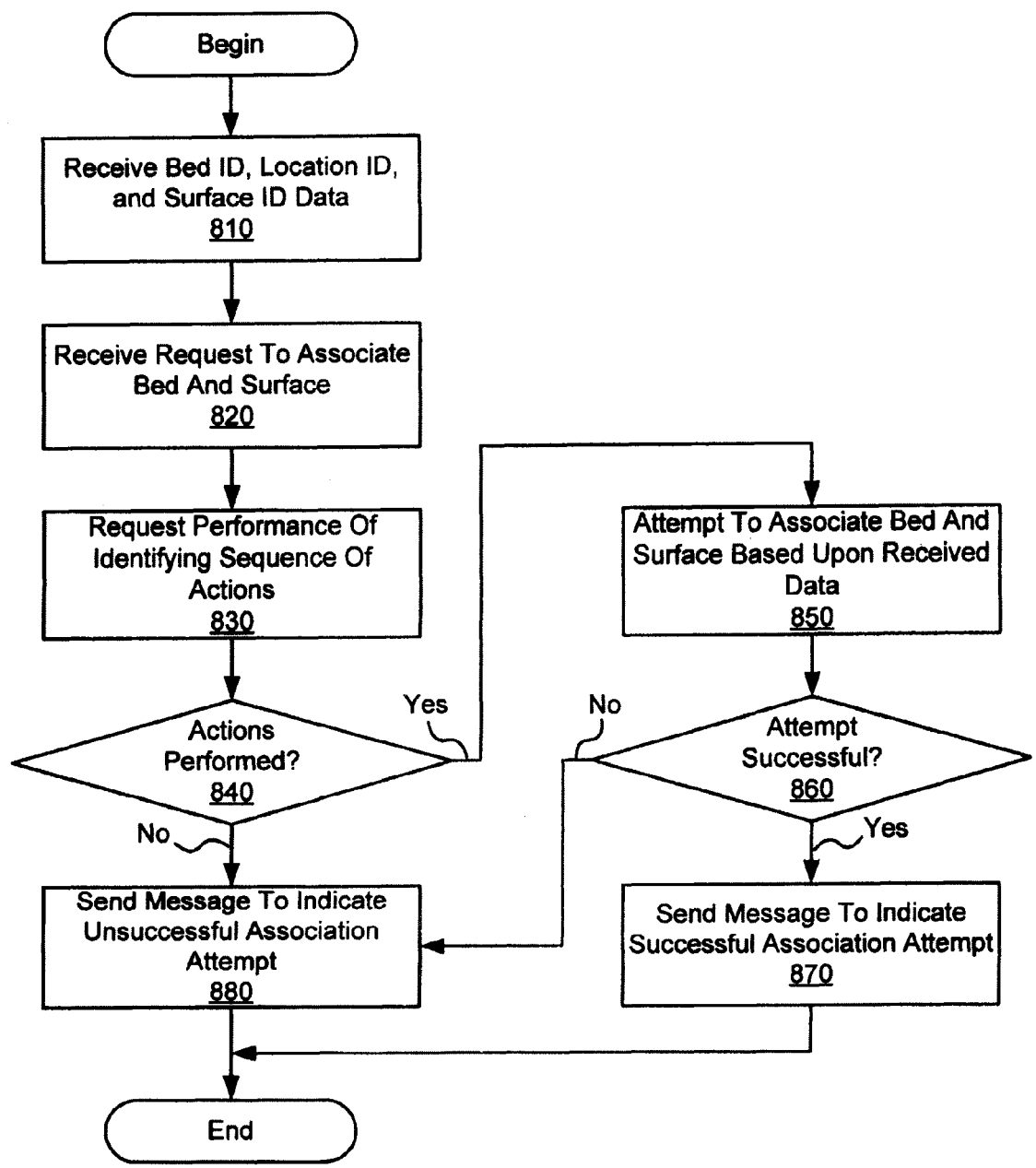
FIG. 8 is a flowchart of another embodiment of a support surface association method which may be implemented by a computing device of the healthcare facility in order to provide a support surface association service that associates beds and support surfaces of the healthcare facility to one another.

A technique to resolve such conflicts in an automated manner is incorporated in the surface association method presented in FIG. 8. The surface association method of FIG. 8 permits a healthcare facility to deploy fewer location transmitters 332 and perform less tuning of location transmitters 332 and location receivers 342, 362 since the technique resolves conflicts in an automated or semi-automated manner.

As shown, the computing device 4 as indicated at block 810 may receive bed ID data and location ID data from beds 22 of the healthcare facility and may receive surface ID data and location ID data from support surfaces 46 of the healthcare facilities in a manner similar to block 710 above. As indicated at block 820, the computing device 4 may receive a request to associate a bed 22 and surface 46 with one another in a manner similar to block 720 above.

In response to receiving the surface association request, the computing device 4 may request that the caregiver perform a predetermined sequence of actions on the bed 22 and/or the surface 46 to identify the bed 22 and surface 46 to be associated with one another as indicated at block 830. The identifying sequence of actions in one embodiment is selected such that the sequence of actions is unlikely to otherwise occur during normal operation of the bed 22 or surface 46 to be associated. Thus, the computing device 4 may identify a bed 22 and/or surface 46 of a surface association request based upon receipt of status data that indicates the occurrence of the identifying sequence of actions.

At block 830, the computing device 4 may provide the caregiver with the request to perform the identifying actions using various mechanisms. The computing device 4 may transmit one or more control messages to a bed 22 or bed(s) 22 having the same location ID as the received surface association request in order to cause user interface(s) 50 of the bed(s) 22 to display the request. The computing device 4 may transmit one or more control messages to surface(s) 46 having the same location ID as the received surface association request in order to cause the user interface(s) 360 to display the request. As another option, the computing device 4 may send the control messages to the device (e.g. bed 22 or surface 46) that initiated the surface association request in order to cause the respective user interface 50, 360 to display the request. As yet another option, the computing device 4 may send a message (e.g. audio message and/or text message) to a pager, PDA or other type of wireless communication device such as Vocera® handsets or telephone handsets that have bidirectional voice communication capability and that may have text messaging capability of a caregiver located near the bed 22 or surface 46 that initiated the request. The computer device 4 may also send an audio message and/or text message to an audio station of a bed station 24 located near the multiple beds 22 or surface 46 that are possibly the ones that initiated the request.

As indicated at block 840, the computing device 4 may detect the identifying sequence based upon whether status data received from the bed 22 and/or surface 46 indicates the performance of the identifying sequence of actions. In one embodiment, the computing device 4 determines that identifying sequence of actions were performed only if received from a bed 22 and/or a surface 46 having the same location ID data as the surface association request. As mentioned above, multiple beds 22 and/or surfaces 46 may be located sufficiently close to the same location transmitter 332 of the healthcare facility to result in multiple beds 22 and/or surfaces 46 receiving and then re-transmitting the same location ID data. Thus, the healthcare facility may have multiple beds 22 and/or surfaces 46 with the same location ID data as the surface association request. However, the computing device 4 may identify the one bed 22 and/or surface 46 to be associated based upon status data identifying the predetermined sequence of actions and such actions being associated with a bed 22 and/or surface 46 with the same location ID data. In this manner, computing device 4 may support multiple surface association requests and appropriately match beds 22 and surfaces 46 of different overlapping requests within the healthcare facility.

If the sequence of actions is received from an appropriate bed 22 and/or surface 46, the computing device 4 may attempt to associate the identified bed 22 and surface 46 as indicated at block 850. The computing device 4 at block 860 may determine whether the attempt to associated the bed 22 and surface 46 succeeded in a manner similar to block 740 above. In manner similar to block 830 above, the computing device 4 at block 870 may provide the person requesting the association with an indication of the successful association. Conversely, if the predetermined sequence of actions was not received within a predetermined period (e.g. 20 seconds) or the attempted association failed, the computing device as indicated at block 880 may provide the person requesting the association with an indication of the unsuccessful association of the bed. Again, the computing device 4 may provide the indication in a manner similar to block 830 above.

Figure 9:
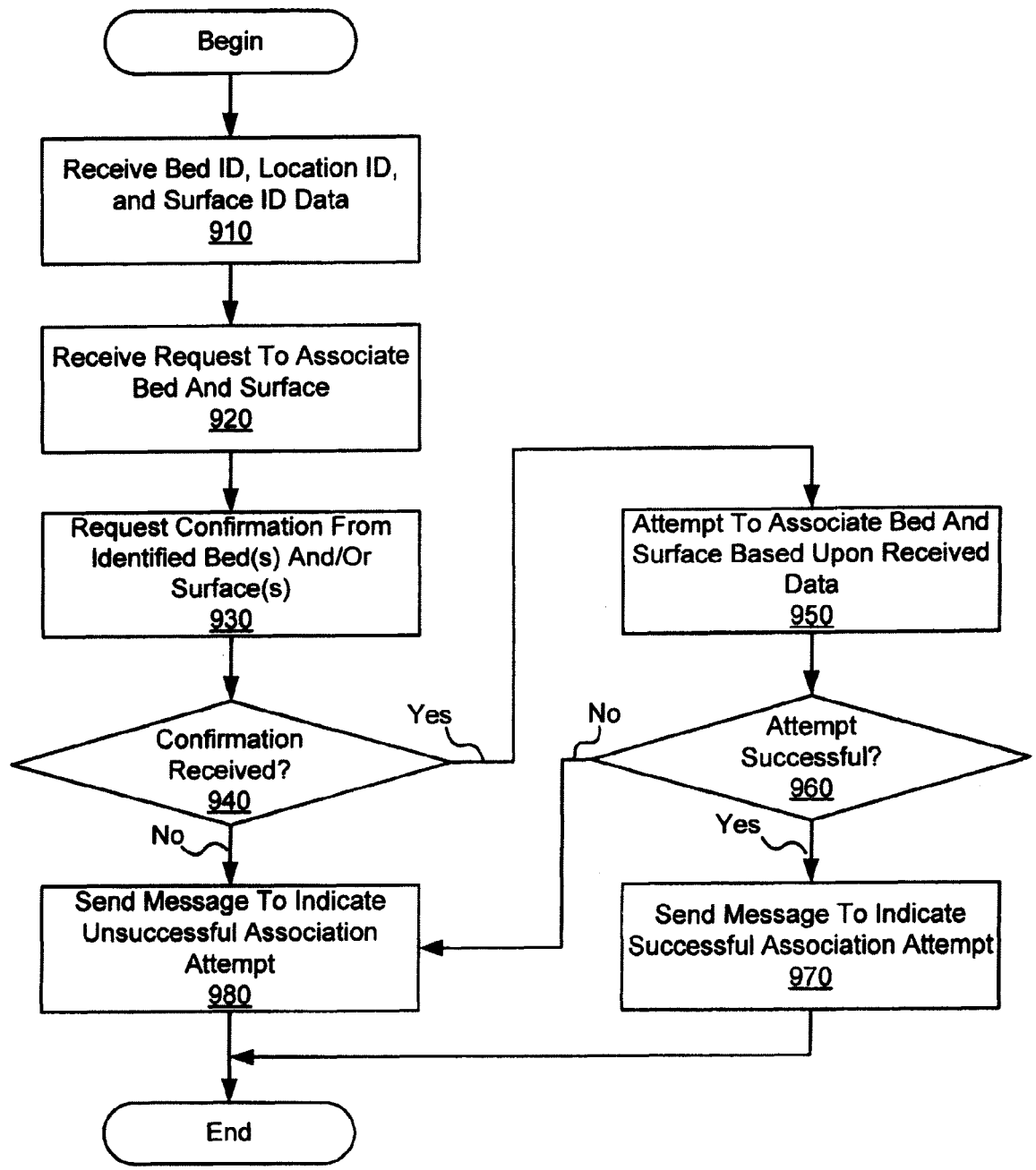
FIG. 9 is a flowchart of yet another embodiment of a support surface association method which may be implemented by a computing device of the healthcare facility in order to provide a support surface association service that associates beds and support surfaces of the healthcare facility to one another.

Another technique to resolve such conflicts in an automated manner is incorporated in the surface association method presented in FIG. 9. As indicated at block 910, the computing device 4 may receive bed ID data and location ID data from beds 22 of the healthcare facility and may receive surface ID data and location ID data from support surfaces 46 of the healthcare facilities in a manner similar to block 710 above. In a manner similar to block 720 above, the computing device 4 may receive a request to associate a bed 22 and surface 46 with one another as indicated at block 920.

In response to receiving the surface association request, the computing device 4 as indicated at block 930 may request that the caregiver perform a predetermined sequence of actions on the bed 22 and/or the surface 46 to confirm which bed 22 and/or surface 46 to be associated. In one embodiment, the computing device 4 in response to receiving the surface association request from the surface 46 transmits a control message to the bed or beds 22 having the same location ID as the surface 46. Similarly, the computing device 4 in response to receiving the surface association request from a bed 22 transmits a control message to the surface or surfaces 46 having the same location ID as the bed 22. As explained above, the healthcare facility may have multiple beds 22 and/or surfaces 46 within range of a location transmitter 332, thus resulting in multiple beds 22 and/or surfaces 46 having the same location ID. In such a case, the computing device 4 may send the request to multiple beds 22 or surfaces 46.

As indicated at block 940, the computing device 4 may determine based upon status data received from the bed 22 and/or surface 46 whether a confirmation from a caregiver was received. In one embodiment, the caregiver performs the actions on the bed 22 or surface 46 to be associated thus identifying the one device from potentially several devices to be associated. The computing device 4 in one embodiment determines that confirming actions were performed only if received from a bed 22 and/or a surface 46 having the same location ID data as the surface association request.

If confirmation is received, the computing device 4 as indicated at block 950 attempts to associate the identified bed 22 and surface 46. As indicated at block 960, the computing device 4 determines whether the attempted association was successful. If successful, the computing device provides the person requesting the association with an indication of the successful association as indicated at block 970. Conversely, if the predetermined sequence of actions was not received within a predetermined period (e.g. 20 seconds) or the attempt was otherwise unsuccessful, the computing device may provide the person requesting the association with an indication of the unsuccessful association of the bed as indicated at block 980. It should be appreciated that the computing device 4 may provide the user with a successful indication or an unsuccessful indication using numerous different approaches as mentioned above in regard to blocks 750 and 760.

The above surface association services may be used by a nurse call system to control the operation of a bed 22 and its associated surface 46. In one embodiment, one or more computing devices 4, such as those implementing a nurse call system, are operable to send command or control messages through the network infrastructure to beds 22 and surfaces 46 to control some aspect of the operation of beds 22 and surfaces 46. The words "command" and "control" are intended to be interchangeable according to this disclosure and each is intended to have the broad meaning of both. Therefore, such computing devices 4 may be operable to receive bed status data from bed 22, process it, and then, based on the bed status data from bed 22, transmit a control words or messages to bed 22 and/or surface 46. For example, if the bed status data from bed 22 indicates that a CPR release handle of the bed 22 has been pulled, then the control message to the support surface 46 associated with the bed 22 may result in the support surface 46 going into a max inflate mode to harden the air bladders in surface 46 in preparation for CPR being performed on the patient or, alternatively, the control message may result in support surface 46 completely deflating so that the patient is supported by the support deck 47 underlying the support surface 46 in preparation for CPR being performed on the patient.

As another example, if the bed status data from bed 22 indicates that casters of the hospital bed have been unbraked, then the command message to the associated support surface 46 may indicate that a therapy, such as lateral rotation therapy, alternating pressure therapy, percussion therapy, etc. should be stopped in preparation for the bed 22 being moved to a new location. As another example, one or more computing devices 4 may be operable to receive the surface status data from support surface 46, process it, and then, based on the surface status data, transmit a control message to bed 22. For example, if the surface status data indicates that lateral rotation therapy is active, then the control message to bed 22 may lock out a head section motor to prevent the head section of the bed 22 from being raised during the lateral rotation therapy. Computing device 4 may be configured to send surface status data to any other computer devices 4 coupled to network 10.

While embodiments are disclosed, the description is not intended to be construed in a limiting sense. Various modifications of the described embodiments, as well as other embodiments which are apparent to persons skilled in the art, are deemed to lie within the spirit and scope of the appended claims.

What is claimed is:

1. A patient support system comprising
a bed having bed control circuitry, a bed ID, and a first network interface,
a support surface supported on the bed and having support surface control circuitry, a surface ID, and a second network interface, and
a location transmitter device spaced from the bed, spaced from the bed control circuitry, spaced from the support surface, and spaced from the support surface control circuitry, the location transmitter device having a location ID that is transmitted from the location transmitter to the bed control circuitry and to the surface control circuitry,
wherein the bed control circuitry operates to transmit the bed ID and the location ID from the bed via the first network interface to at least one access point of a network,
wherein the surface control circuitry operates to transmit the surface ID and the location ID from the surface via the second interface to the at least one access point of the network,
wherein the bed or the support surface has a user interface including a display screen on which is displayed a request to perform at least one identifying action using a mechanism of the bed or the surface other than the display to confirm association of the bed or surface to the location or to confirm association of the bed and surface to each other.

2. The patient support system of claim 1, further comprising a remote computer device that receives the bed ID and location ID and that receives the surface ID and the location ID, the computer device being operable to associate the bed having the bed ID and the surface having the surface ID to a location corresponding to the location ID.

3. The patient support system of claim 2, wherein the remote computer device has a user interface that is operable by a user to confirm the association of the bed and surface to the location.

4. The patient support system of claim 2, wherein the remote computer device has a user interface that is operable by a user to unassociate the bed and the surface from the location.

5. The patient support system of claim 1, wherein the bed has a first user interface to command operation of bed functions and the surface has a second user interface to command operation of surface functions.

6. The patient support system of claim 5, wherein data regarding the manner in which the bed functions are commanded by the first user interface of the bed is transmitted by the bed control circuitry from the bed via the network interface.

7. The patient support system of claim 5, wherein the data regarding the manner in which the surface functions are commanded by the second user interface of the support surface is transmitted by the surface control circuitry from the support surface via the network interface.

8. The patient support system of claim 1, wherein the bed has a housekeeping button that is pressed to signal the bed control circuitry to transmit a housekeeping request from the bed via the network interface.

9. The patient support system of claim 1, wherein the first network interface is communicatively coupled to a network via a wired communications link.

10. The patient support system of claim 1, wherein the first network interface is communicatively coupled to a network via a wireless communications link.

11. The patient support system of claim 1, wherein the second network interface is communicatively coupled to a network via a wired communications link.

12. The patient support system of claim 1, wherein the second network interface is communicatively coupled to a network via a wireless communications link.

13. The patient support system of claim 1, wherein the bed has an indicator to indicate a status regarding whether the bed is successfully connected to a network via the network interface.

14. The patient support system of claim 13, wherein the indicator is mounted to a base frame of the bed.

15. The patient support system of claim 13, wherein the indicator is mounted to a siderail of the bed.

16. The patient support system of claim 1, wherein the bed control circuitry is configured to receive control commands from a remote computer via the first network interface to control at least one bed function.

17. The patient support system of claim 1, wherein the surface control circuitry is configured to receive control commands from a remote computer via the second network interface to control at least one support surface function.

* * * * *